(12) United States Patent
Schiebler

(10) Patent No.: US 7,582,089 B2
(45) Date of Patent: Sep. 1, 2009

(54) MULTI-USE LINKAGE DEVICE

(76) Inventor: Mark Schiebler, 70 Cypress La., Maitland, FL (US) 32751

( * ) Notice: Subject to any disclaimer, the term of this patent is extended or adjusted under 35 U.S.C. 154(b) by 349 days.

(21) Appl. No.: 11/443,972

(22) Filed: May 31, 2006

(65) Prior Publication Data

US 2006/0214069 A1    Sep. 28, 2006

Related U.S. Application Data

(62) Division of application No. 10/635,889, filed on Aug. 6, 2003, now Pat. No. 7,164,360.

(60) Provisional application No. 60/403,722, filed on Aug. 14, 2002.

(51) Int. Cl.
*A61B 17/56* (2006.01)
(52) U.S. Cl. .................. 606/74; 606/148; 606/151; 248/74.3; 24/16 PB; 292/307 A
(58) Field of Classification Search ............. 248/74.3, 248/68.1, 72; 24/16 PB; 606/74, 151, 218, 606/309, 60, 916, 71, 216; 292/307 R, 315, 292/316, 317, 318, 319, 322, 323, 325, 326, 292/307 A; 206/343
See application file for complete search history.

(56) References Cited

U.S. PATENT DOCUMENTS

| | | | |
|---|---|---|---|
| 3,570,497 A | 3/1971 | Lamole | |
| 3,712,655 A * | 1/1973 | Fuehrer | ............ 292/321 |
| 3,926,193 A * | 12/1975 | Hasson | ............ 606/218 |
| 3,973,292 A | 8/1976 | Bonnet | |
| 4,119,091 A * | 10/1978 | Partridge | ............ 606/74 |
| 4,161,348 A * | 7/1979 | Ulrich | ............ 385/115 |
| 4,202,349 A | 5/1980 | Jones | |
| 4,272,670 A | 6/1981 | Docx | |
| 4,306,745 A | 12/1981 | Wenk | |
| 4,506,415 A | 3/1985 | Swift | |
| 4,730,615 A * | 3/1988 | Sutherland et al. | ............ 606/215 |
| 4,825,156 A | 4/1989 | Read | |
| 5,079,540 A | 1/1992 | Narlow et al. | |
| 5,088,158 A | 2/1992 | Burkholder | |
| 5,190,545 A * | 3/1993 | Corsi et al. | ............ 606/74 |
| 5,219,194 A * | 6/1993 | Trent et al. | ............ 292/307 R |
| 5,330,503 A * | 7/1994 | Yoon | ............ 606/223 |
| 5,337,503 A | 8/1994 | Goby | |
| 5,338,209 A | 8/1994 | Brooks et al. | |
| 5,524,463 A | 6/1996 | Schenkel et al. | |
| 5,524,945 A * | 6/1996 | Georgopoulos et al. | ............ 292/307 A |
| 5,549,619 A * | 8/1996 | Peters et al. | ............ 606/151 |
| 5,632,753 A * | 5/1997 | Loeser | ............ 606/151 |
| 5,665,089 A * | 9/1997 | Dall et al. | ............ 606/71 |
| 5,766,218 A * | 6/1998 | Arnott | ............ 606/151 |
| 5,802,888 A | 9/1998 | Parsons | |

(Continued)

*Primary Examiner*—Anita M King
(74) *Attorney, Agent, or Firm*—Terry M. Sanks, Esq.; Beusse Wolter Sanks Mora & Maire, P.A.

(57) ABSTRACT

A linkage device that can be connected with other linkage devices and to itself, the linkage device comprising a strip having a first end and a second end, a closure hub attached to the first end of the strip and having an opening to receive a second end and a locking mechanism within the closure hub, a connecting surface protruding from the strip operable to secure the second end within a closure device, and a tampering detection device connected to the linkage device.

15 Claims, 23 Drawing Sheets

U.S. PATENT DOCUMENTS

| | | |
|---|---|---|
| 5,864,290 A | 1/1999 | Toyomi et al. |
| 5,969,613 A | 10/1999 | Yeager et al. |
| 5,984,963 A | 11/1999 | Ryan et al. |
| 6,050,998 A | 4/2000 | Fletcher |
| 6,219,887 B1 | 4/2001 | Parsons |
| 6,561,350 B1 * | 5/2003 | Ueno ......................... 206/343 |
| 6,938,305 B2 | 9/2005 | Garver |
| 7,164,360 B2 * | 1/2007 | Schiebler ................. 340/572.9 |
| 2002/0177863 A1 * | 11/2002 | Mandel et al. .............. 606/158 |

* cited by examiner

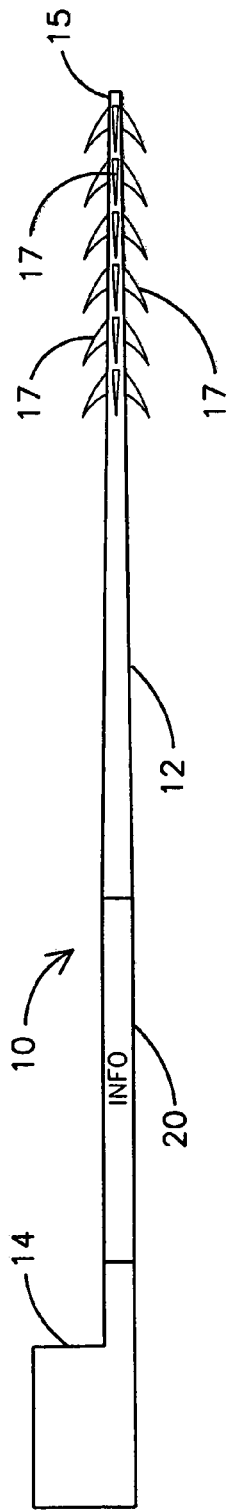
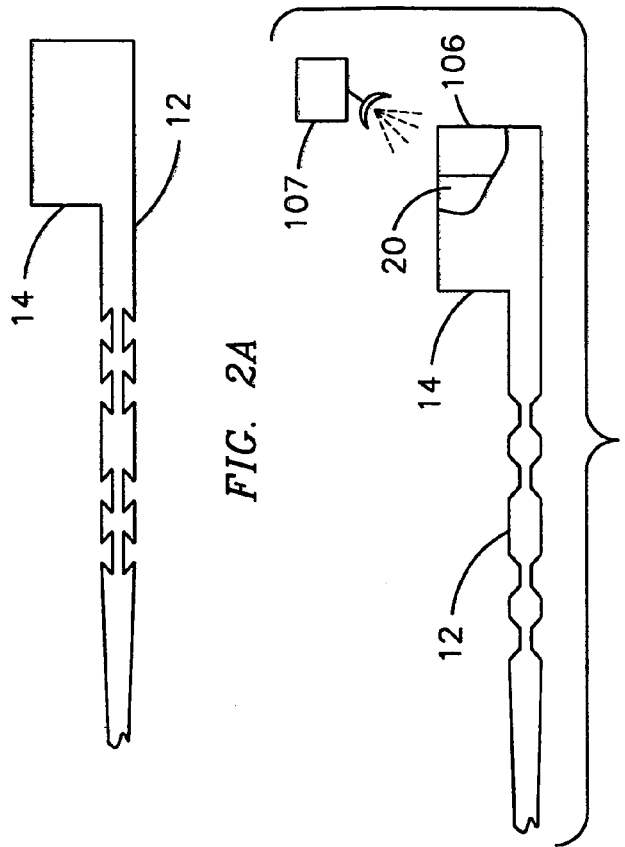
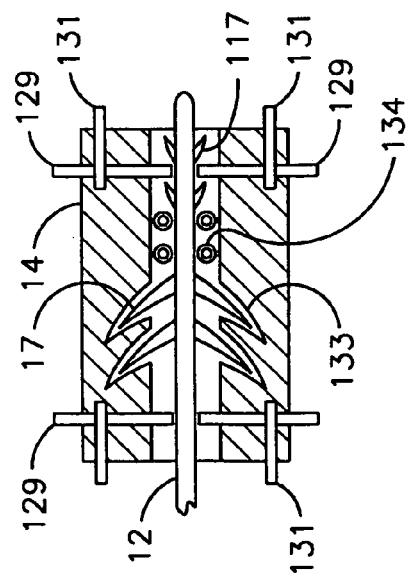

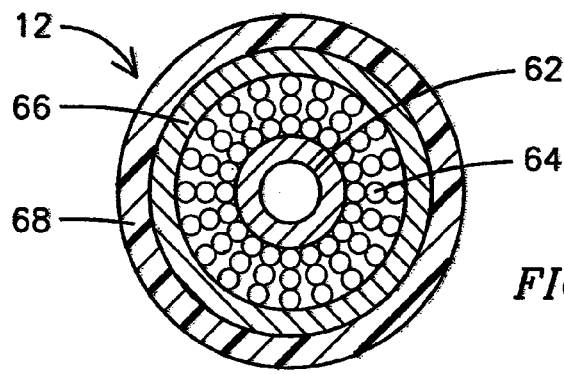
FIG. 5
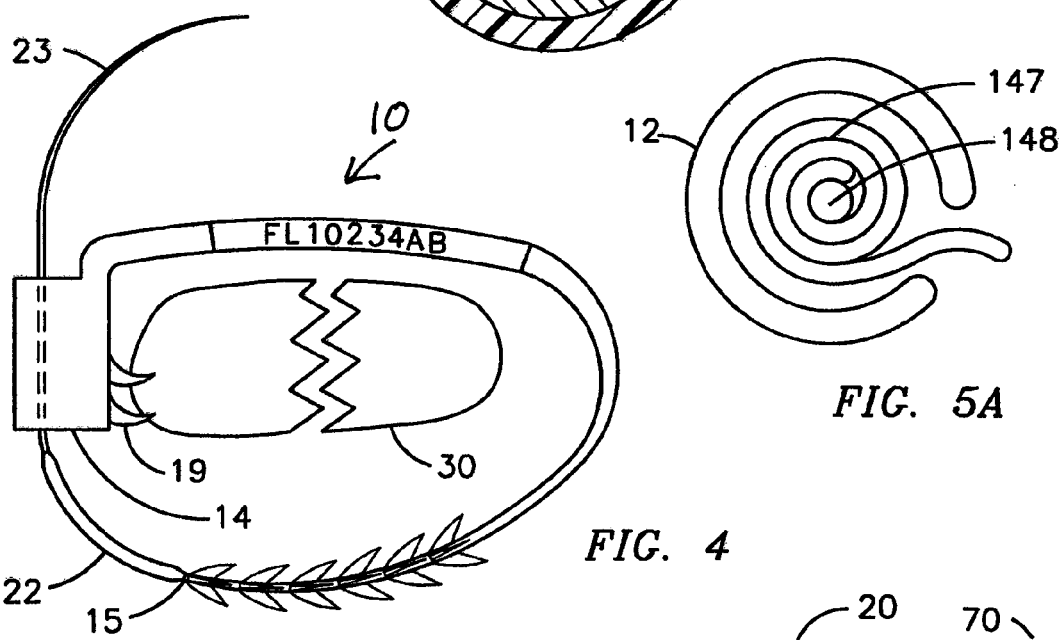
FIG. 5A
FIG. 4
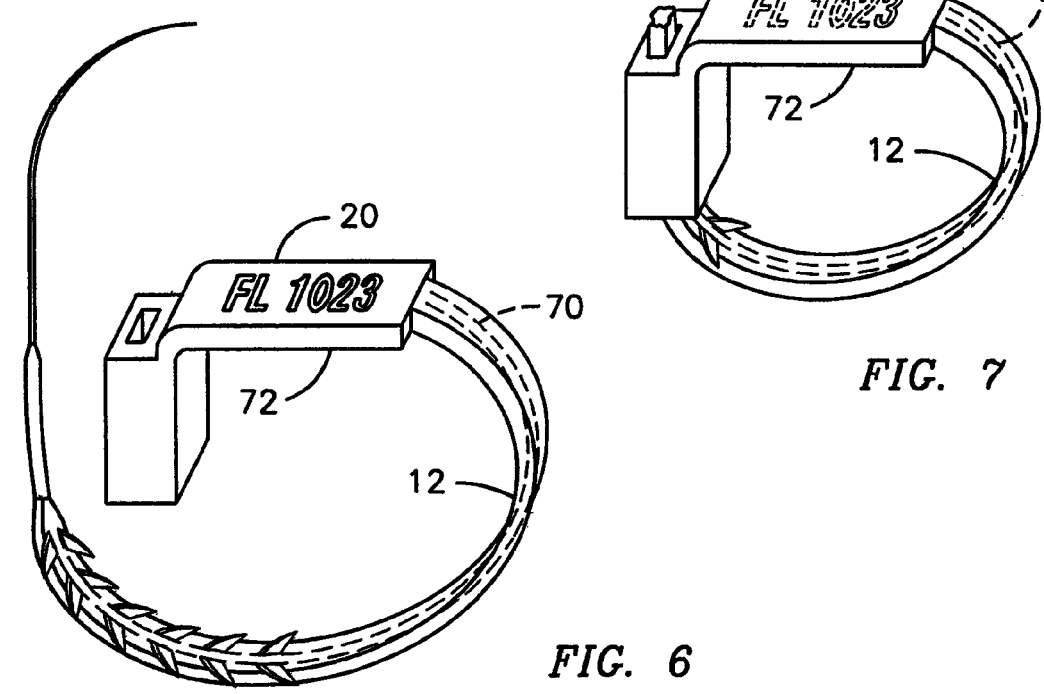
FIG. 7
FIG. 6

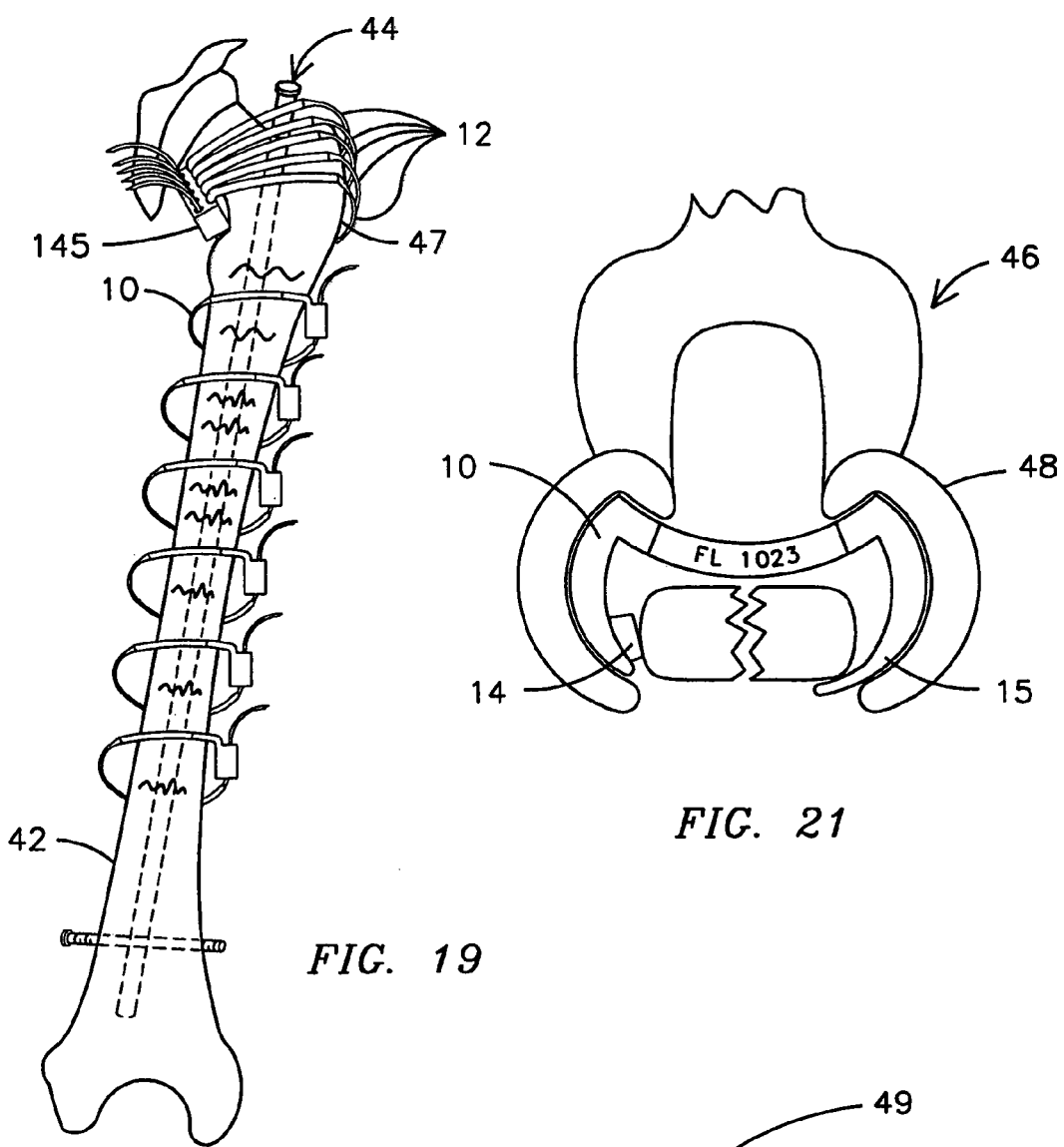
FIG. 19
FIG. 21
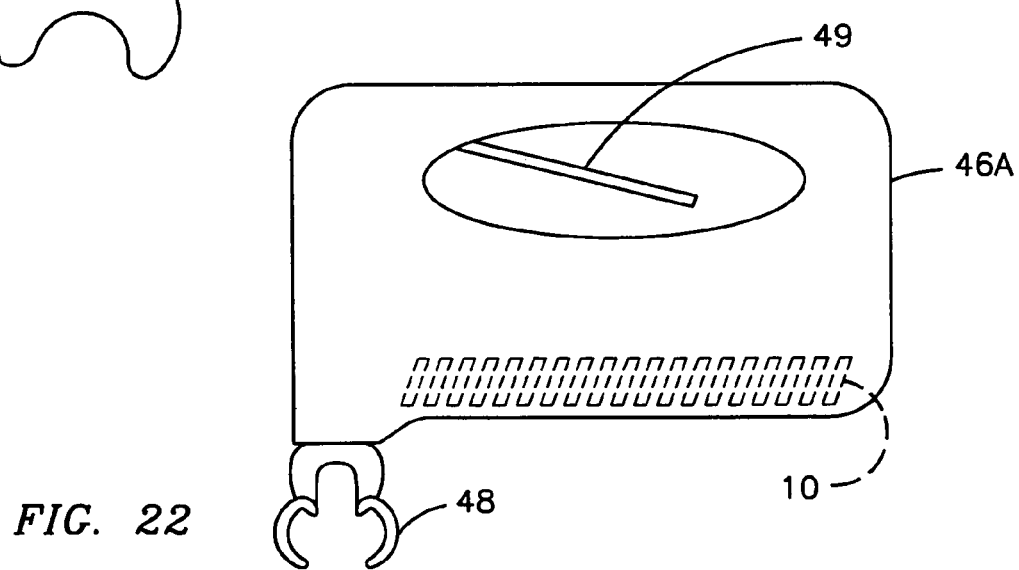
FIG. 22

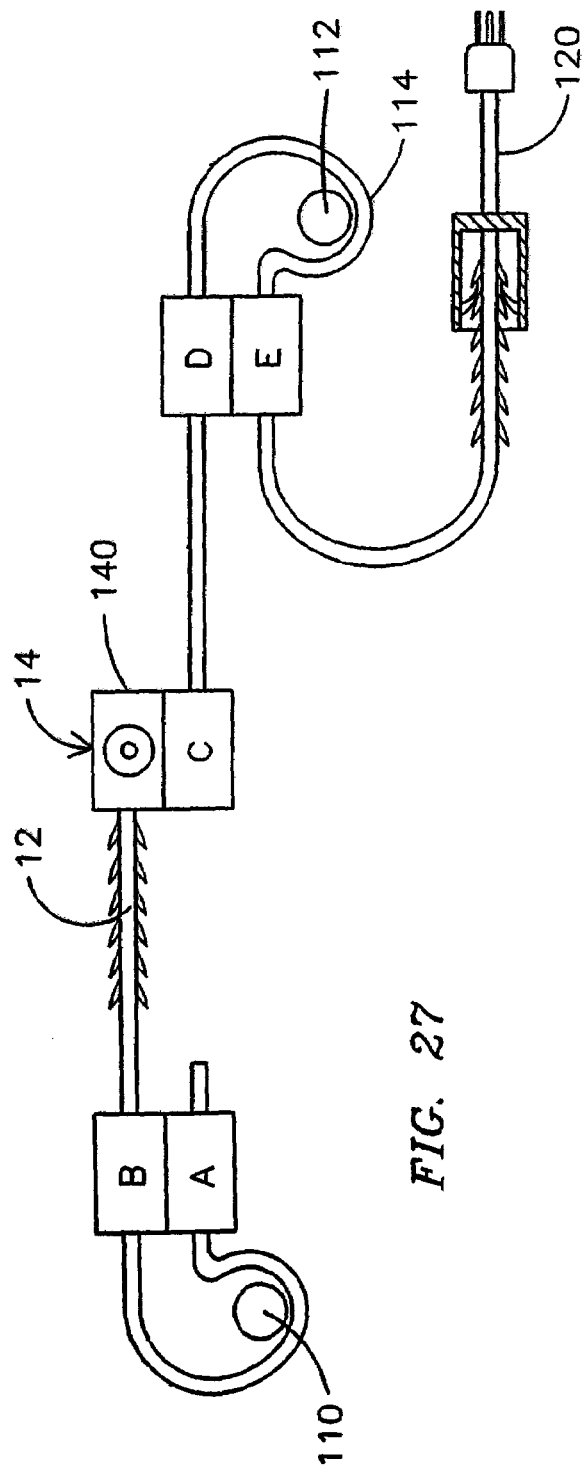
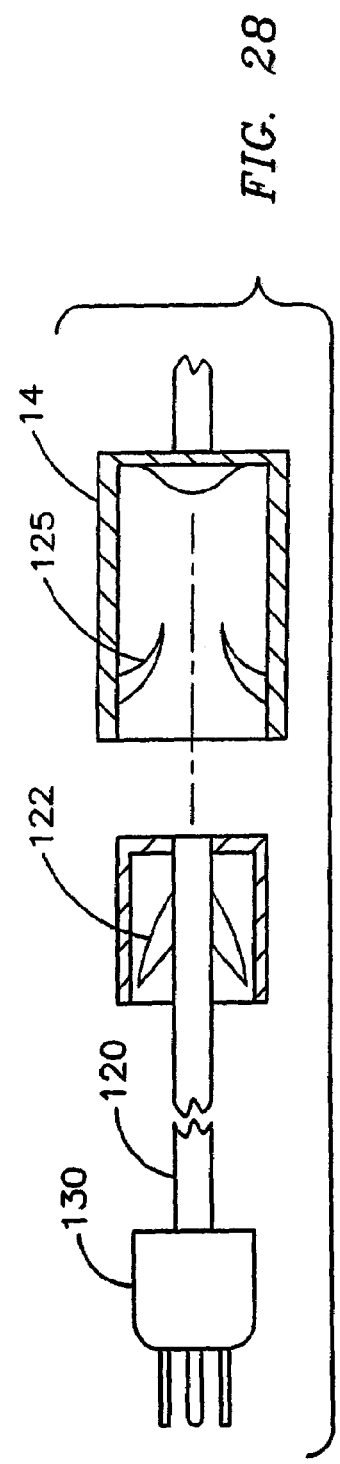
FIG. 27
FIG. 28

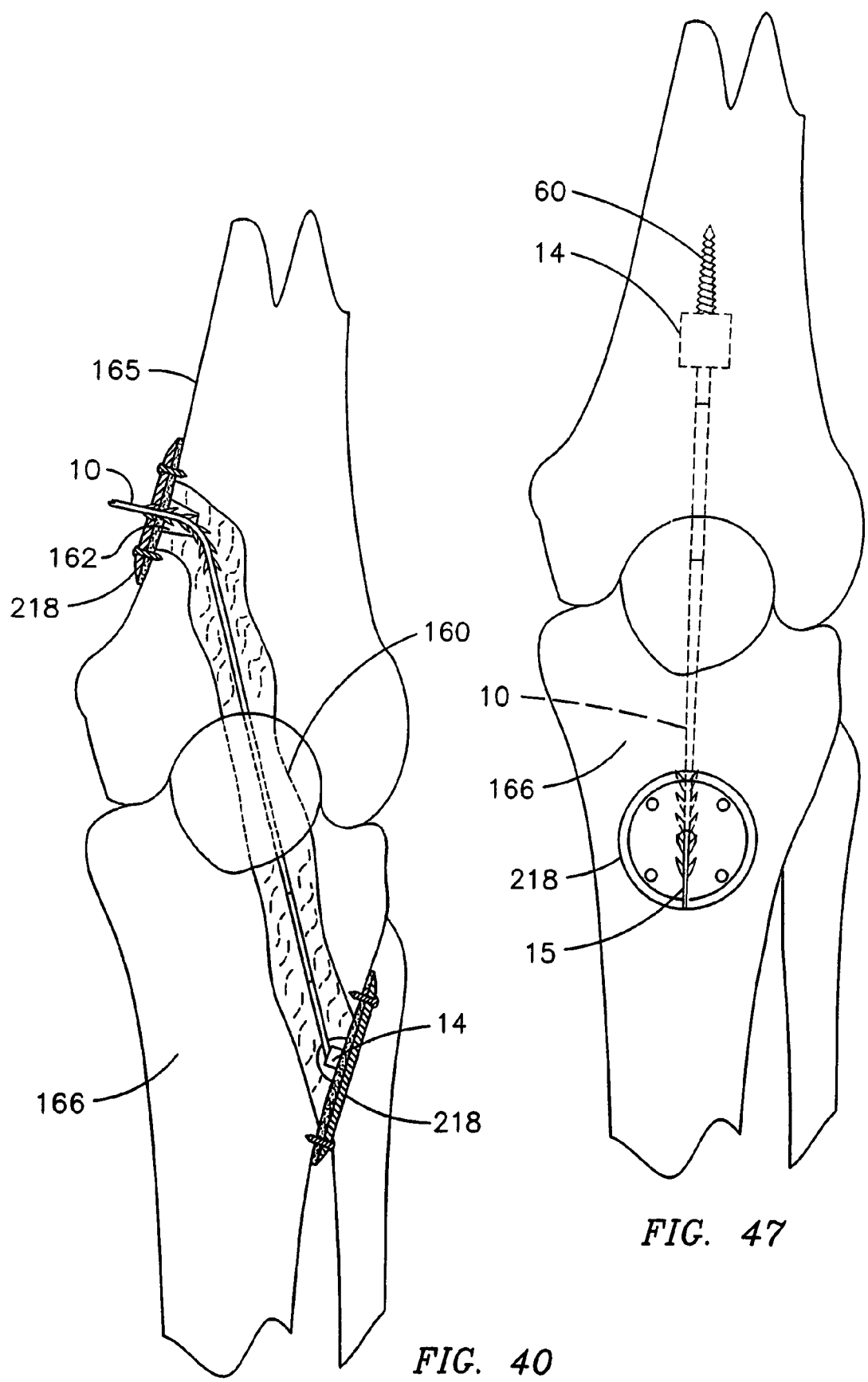

MULTI-USE LINKAGE DEVICE

This application is a Divisional of application Ser. No. 10/635,889, filed on Aug. 6, 2003, now U.S. Pat. No. 7,164,360 which claims priority of Provisional Patent Application Ser. No. 60/403,722, filed on Aug. 14, 2002, which are incorporated herein by reference in their entirety.

BACKGROUND OF THE INVENTION

This invention relates to a tie, and more particular to a linkage or binding device with a plurality of uses where such uses include being able to obtain use specific information from the closure device and being able to determine whether the device has been tampered with or has failed and to transport information and/or material through it to another location.

Plastic ties are well known in the prior art and have been used for a variety of uses, such as security seals, and binding devices to hold objects together. In recent years, plastic ties are now used in place of metal handcuffs especially when a plurality of arrests is made at a given time where a police officer needs to handcuff more than one individual.

Security seals are used to insure that containers are not opened, or tampered with during shipping. Even though security seals were primarily constructed of metal, plastic seals later became popular since unlike metal straps, plastic seals did not rust or corrode. Additionally, plastic seals are cheaper to produce. Nevertheless, current plastic seals also have drawbacks. For example it is believed that heat or glue can be used to defeat a plastic seal. Specifically, plastic seals, or ties have ratchet serrations or protrusions, on a surface, which lock into a socket mechanism at one end of the tie. The socket mechanism has been known to be defeated by using a thin pin to release the ratchet serrations from the socket mechanism. The ratchet serrations are then later re-reconnected to the socket mechanism with glue. Thus a user may not know that the tie had been defeated or tampered with. Likewise, heating the plastic, such as in hot water, has also been known to defeat the locking features, where the segment of the strap held in place within the socket mechanism loses its rigidity and is able to be removed from the socket. Having a seal or fastener that is not as easy to defeat and where an inspector can readily determine whether the device has been tampered with is desirable.

To assist with the healing process after certain medical procedures, surgical wire is usually used, such as to hold a separated bone together. For example, during an operation where a surgeon needs access to a patient's heart, such as for a heart valve replacement or coronary artery bypass, a median sternotomy procedure is performed where the sternum is typically separated longitudinally down the center of the bone, from the manubrium to the xyphoid, and then spread apart so that a surgeon has an unobstructed access to the heart for surgical exposure. Once the operation is complete, surgical wire, typically monofilament stainless steel suture, is used to immobilize the separated bone of the sternum so that the bone may begin its healing process.

The surgical wire, which has limited flexibility, is placed around both halves of the divided sternum. It is then threaded between ribs in the corresponding intercostal spaces and through the intercostal muscles on either side of the sternum. Once placed around the back of the sternum, the ends of the wire are secured on the front side, where the ends are twisted to pull together the halves of the sternum. Excess wire is then cut away and the twisted end is folded down onto the sternum.

After the wire is in place, it is not removed, unless there is another operation. Depending on how much skin and fat covers the sternum, a patient may have ridges showing through his or her skin from the surgical wire. These ridges may be uncomfortable when touched and also look abnormal, while also remaining as a constant reminder of the surgery. Additionally, the wire may later erode through the skin, and cause a chronic draining sinus or osteomyelitis of the sternum. In some cases the sternum has to be completely removed due to infection. Due to the physical characteristics of the wire, twisting the wire may increase the cold work in the wire, which makes it more brittle thus increases the probability that it may break. In fact, a majority do eventually break.

Situations arise where a doctor may need to know information about a prior surgery or a patient's prior condition. If the patient does not readily have the information available, the doctor may have to request the information from another hospital and/or another doctor, possibly located in another state or country. An emergency room situation is one instance where obtaining such information immediately may be paramount. Thus having the information provided on the binding device would be beneficial not only to the doctor, but to the patient as well.

BRIEF DESCRIPTION OF THE INVENTION

This invention is directed to a linkage, or binding, device where information can be collected, received or transported through the binding device. Such examples of information includes, but is not limited to, who installed the device, whether the device has been tampered with, or whether the device has failed. The invention is further directed to a device that can be used in a plurality of applications ranging from medical uses to industrial uses.

In one preferred embodiment of the present invention a linkage device is disclosed. The linkage device is comprised of a strip, a hub, a connecting surface protruding from the strip to provide a connecting surface to the hub, and a tampering detection device connected to or imbedded in the binding device. An application distinct tag signifying a specific use for the linkage device can also be part of the linkage device.

In another preferred embodiment a linkage system is disclosed. The linkage system includes a linkage device and an insertion device for placing the linkage device around an object to bind, such as a bone. Another preferred embodiment is a linkage system having a linkage device and a detection device that can read information contained on an application distinct tag.

BRIEF DESCRIPTION OF THE DRAWINGS

The invention itself, both as to organization and method of operation, may best be understood by reference to the following description in conjunction with the accompanying drawings in which like numbers represent like parts throughout the drawings and in which:

FIG. 1 is an illustration of an exemplary embodiment of the linkage device;

FIG. 2A is an illustration of an exemplary embodiment of the linkage device before being expanded;

FIG. 2B is an illustration of an exemplary embodiment of the linkage device after being expanded;

FIG. 3 is another illustration of an exemplary embodiment of a closure hub engaging a strip;

FIG. 4 is an illustration of an exemplary embodiment of the linkage device being placed around a bone, such as sternal segments;

FIG. 5 is an illustration of an exemplary embodiment of a cross sectional view of a strip (first end) of the linkage device;

FIG. 5A is an illustration of an exemplary embodiment of a cross sectional view of a strip where a material is spooled within;

FIG. 6 is an illustration of an exemplary embodiment of the linkage device with an air channel and a reservoir;

FIG. 7 is an illustration of an exemplary embodiment of the linkage device where an illumination material has left the reservoir;

FIG. 19 is an illustration of an exemplary embodiment of a plurality of linkage devices around a long bone;

FIG. 21 is an illustration of an exemplary embodiment of an insertion end of another insertion device;

FIG. 22 is an exemplary embodiment of a side view of the insertion device disclosed in FIG. 21;

FIG. 27 is an illustration of an exemplary embodiment of a plurality of the linkage devices daisy-chained together and illustrating a motorized closure hub;

FIG. 28 is an illustration of an exemplary embodiment of an electric socket adapter;

FIG. 40 is an illustration of an exemplary embodiment of the linkage device tunneled within a knee, such as a posterior cruciate ligament repair;

FIG. 47 is an illustration of an exemplary embodiment of a drill bit being used to anchor a linkage device in a bone (internal trabecular bone anchor)

DETAILED DESCRIPTION OF THE INVENTION

Figure 8:
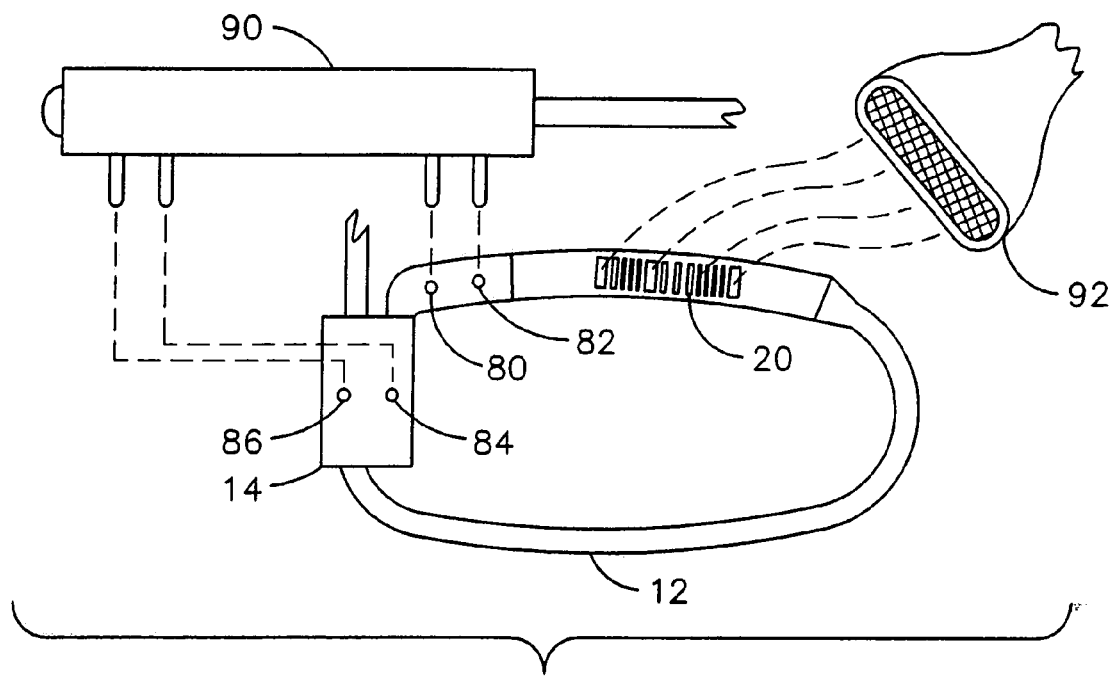
FIG. 8 is an illustration of an exemplary embodiment of the linkage device with a tamper and/or information detection device.

With reference to the figures, exemplary embodiments of the invention will now be described. The scope of the invention disclosed is applicable to a plurality of linking, bindings, fasteners, closures, ties, or other connecting devices used to hold an object or objects together or to transport material (or information, energy, photons, etc.) from one location to another. Thus, even though several embodiments are described specific to certain medical devices, this invention is also applicable to other variations of sutures, linkage, and binding devices. Additionally, even though certain embodiments of the invention are disclosed for use with a human, one skilled in the art will readily recognize that this invention is also applicable to animals.

Likewise, even though certain embodiments are also disclosed specific to security devices, this invention is applicable to other closure devices where a user would benefit from being able to make a visual inspection, either with or without an additional instrument, such as a microscope or a photon-detection device, to determine whether the closure device has failed. Such other uses may include but are not limited to, luggage ties to prevent unauthorized entry into luggage or to identify luggage to a traveler via the traveler's ticket, personalized ribbons for wrapped packages at holidays, containers to be cleared, or already cleared, through customs, or to identify cargo at traffic or security check points, such as border crossings.

Additionally, the scope of the present invention is not limited to a single linkage device. The present invention can be connected to other versions of the present invention or variations thereof for other uses where it is not used to bind objects but to transport material or as a structure to support the placement of other structures. The size of the present invention may also vary, since this invention can be sized for use in Micro-Electro-Mechanical Systems (MEMS) technology, or smaller (nano-technology), and up to heavy construction uses, or larger.

As will become clear to one skilled in the art, the elements of the present invention can be imbedded inside of the invention or connected to an outer surface of the invention. For clarification, when connected to or imbedded is used, these terms are meant to address both ways, and other conceivable ways, of putting the present invention together.

FIG. 1 is an exemplary embodiment of the present invention. The invention 10 is a strip 12 of material that is elongated in shape where a first end has a closure device or hub device 14. The strip 12 may be pliable, rigid and/or expandable. The material that comprises the present invention may be biodegradable material or a material that will not deteriorate over time, or a variation where parts may deteriorate whereas other parts will not. With respect to being expandable, in a preferred embodiment the strip has segments which can expand, as illustrated in FIGS. 2A and 2B. In other embodiments, such as those discussed below, the center of the strip may be hollow wherein other components are placed. The elongated shaped segment 12 of the linkage device 10, or strip, can have a plurality of shapes and lengths. For example the cross section of the strip can be cylindrical, triangular, rectangular, and/or any other geometric or non-geometric, shape. The second end 15 of the invention fits within the hub 14. The second end 15 of the invention has protrusions 17, or ridges, extending from the invention so that when the second end 15 engages the closure device 14, the protrusions 17 engage a closing mechanism in the closure device 14 that prevents the second end 15 from being pulled out of the closure hub 14. The protrusions 17 can be located on any surface of the strip. The protrusions 17 may comprise a plurality of shapes such as, but not limited to, shark-tooth ridges, and recessed double ridge back configuration ridges. The protrusions may extend in a plurality of directions from the strip 12. Though the term protrusion is used, the protrusions could be indentions or another form of missing area from a strip wherein the hub 14 will have protrusions to engage the indentions.

As is illustrated in FIG. 3, in one preferred embodiment the strip 12 comprises forward facing protrusions 117 and backward facing protrusions 17. As discussed previously, when placed within the hub 14, the backward facing protrusions 17 engage an inner receiving surface 133 of the hub 14. The hub 14 has a plunger device 129, or devices so that when the strip 12 has engaged the hub 14, the plunger devices 129 are positioned in a locked position, engaging the forward facing protrusions 117. To further prevent tampering, plunger locks 131 are provided to hold the plunger devices 129 in place. As further illustrated, rolling pins, or ball bearings, 134 are located within the hub 14 and in one embodiment are the inner receiving surface that assist with the strip 12 engaging the hub 14. The rolling pins 134 assist the strip 12 in moving freely into the hub 14.

"Viper-teeth" 19, as illustrated in FIG. 4, located near the closure end 14 of the invention or linkage, or binding, device 10, can also be included on the linkage device 10. The viper teeth 19 are used to assist in holding the invention 10 in place. Once positioned around an object the viper teeth 19 help to anchor it, preventing the invention 10 from rotating or sliding around the object 30.

As is further disclosed in FIG. 1, an application distinct tag 20 is also connected to the invention 10. In a preferred embodiment the tag 20 is used to identify a specific use of the linkage device. The application distinct tag, or information data tag 20, may contain information. For example, this information can be deposited in a multiplicity of fashions detectable by instruments or sensation (seeing, hearing, touching, smell, and/or taste) of sentient beings. This information can be visible by the naked eye, by photon activation of the information, and/or by electronic activation wherein the information tag 20 may be on the surface, or imbedded, as illustrated in FIG. 2B, within the linkage device. The information can be encoded where it is accessible at a given frequency located anywhere over a photonic frequency range. As further illustrated in FIG. 2B, the tag 20 may reside on and/or in the hub 14. Examples of photon activation techniques include, but are not limited to, laser, visible light photons, radio frequency photons, X-ray photon, gamma-ray photon, ultraviolet photon, and infrared photons, as illustrated in FIG. 8. With respect to the use of the invention in a living organism, the infrared photons are generated from a patient's own body heat. In each example a receiver 92, or reader, of each respective photon activated information is suited to the type of activation used. In certain situations, the receiver 92 is able to read the tag 20 through other material such as, but not limited to, reading a tag located within a truck, via a Computerized Tomography (CT) scan, or through a large amount of fatty tissue. The information may be tactile, have sound, or a smell as well.

For medical uses, the tag 20 may be made of, but is not limited to, titanium, gold, barium, or another non-Ferro magnetic material, which is X-ray visible, and where an identification code, or data, is placed. In a preferred embodiment, the tag 20 includes markings which can be visible by the naked eye and/or by photon activation of information on the plate, which is then read by a photon reader 92, as illustrated in FIG. 8. The information contained on the tag 20 may be an alpha-numeric code, bar code, imprinted letters, numbers, symbols, digital code, and/or a predefined frequency. The information is just that, to include any way of encoding data that can be retrieved at a later date or concurrent to the data recording, e.g., tactile bumps of Braille. With respect to using X-ray photons to decode information, the reader 92 can be a hand-held reader which can read the information as light photons emanating from an illuminated X-ray film or soft copy of a digital radiograph or CT scan. In another preferred embodiment (not shown) a software reader is built into a computer program to read the information based on a defined region of interest.

With respect to using laser light to decode information, the reader can be a hand held laser, which activates a solution containing a fluorescent material or reflective material inside of the identification plate or tag 20. The symbolic data is then fluoresced, or reflected, back to a visible light photon receiver. When the invention is used for medical uses, such as sutures, such an approach is more useable with thin patients or children, those typically with less than a few centimeters, such as five, of skin and subcutaneous fat covering these sutures.

When using radio frequency to decode information, in a preferred embodiment the tag 20 is a self-regulated chip, which turns off when detecting imaging frequencies from a magnetic resonance imaging (MRI) system. In one embodiment (not shown), this chip is a small coil with a selected set of radio frequency coils that provides a unique signature, such as 28.3 hertz and 32.5 hertz receiver coils imbedded in the plate coil. One skilled in the art will readily recognize other configurations are available with using radio frequency technology and passive identification technology. In other words, the coil's reception frequency can be individualized as a unique signature for each tag 20 much like a radio station has its own frequency designation on the radio frequency spectrum of a radio dial.

Figure 45:
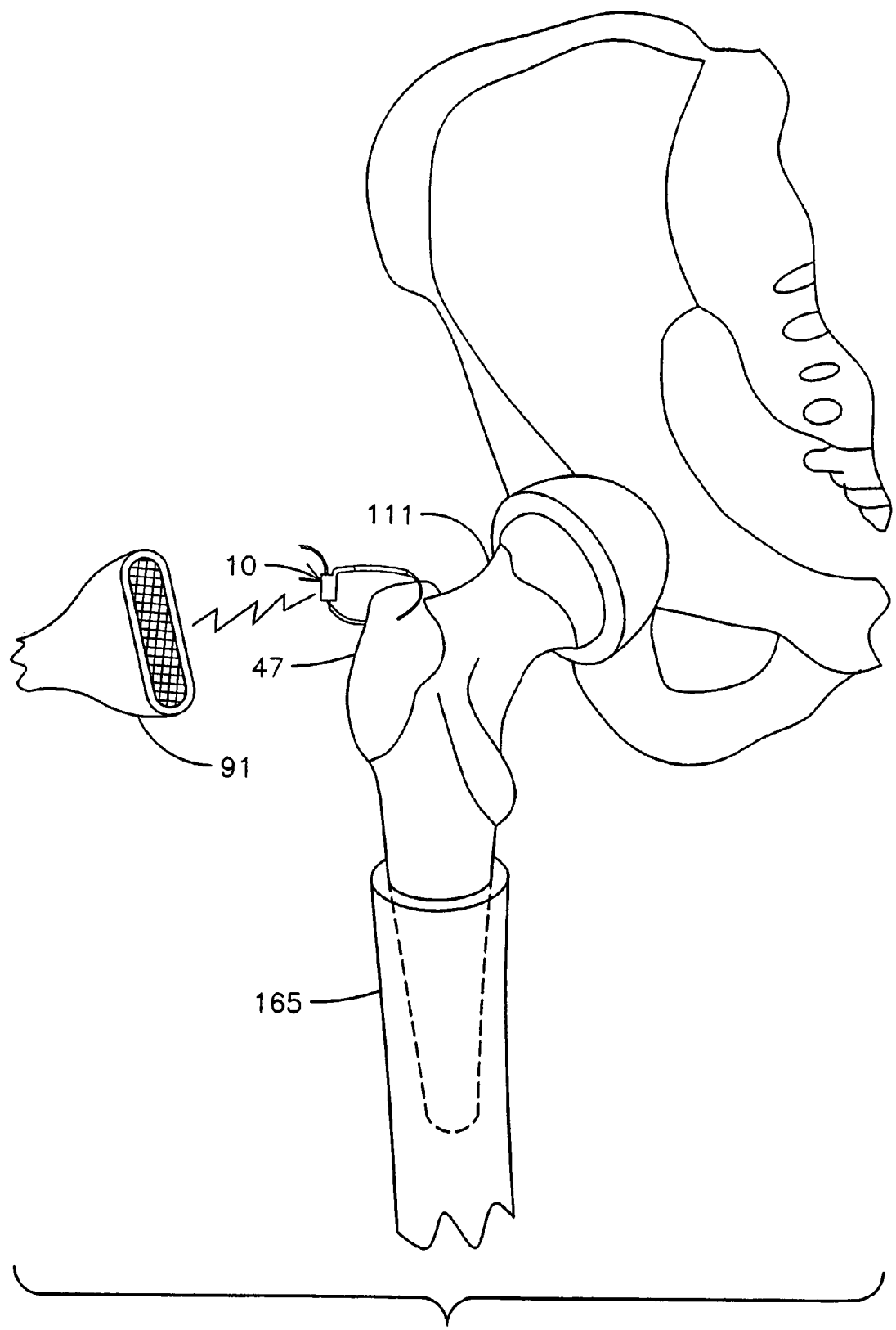
FIG. 45 is an illustration of an exemplary embodiment of the linkage device used with a prosthesis, such as a hip replacement prosthesis.

As illustrated in FIG. 45, a linkage device 10 as discussed above is used as part of a prosthesis 111, such as a hip prosthesis, wherein its unique code, or inductive frequency signature, can be read at a security check point where a metal detector is used, such as at an airport wherein the security guard can readily ascertain that a reason a user is activating the metal detector is because of the metal prosthesis 111. In a preferred embodiment, the security guard would use a detection device 91 that transmits and receives a photonic and/or electronic signal from the linkage device. The use described is not limited to a hip prosthesis. The present invention can also be used with, but not limited to, a shoulder, arm, and/or knee prosthesis as well as with a metal plate fitted within a skull, pacemaker, infusion pump, etc. In a preferred embodiment, the linkage device is provided in the prosthesis wherein the linkage device is insulated and coupled to the prosthetic device and emits a "prosthetic specific" inductive signature. In another preferred embodiment, the linkage device is resistively coupled to the metal in the prosthesis which results in the prosthesis having a specific identity or signature. Though illustrated as being connected to the greater trochanter 47, the linkage device 10 can be integrated into the prosthesis 111.

In another preferred embodiment, such as is illustrated in FIG. 2B, the tag 20 also has its own battery 106 and emits its own radio wave frequency that is used for information storage, access of information, and/or determining a location of the present invention. In another preferred embodiment, the tag 20 is GPS active and gives a signal which can be used to determine the location of the linkage device, such as if necessary to locate a kidnapped child or adult who has a linkage device in or on their possession. The signal may be delivered as a burst signal, wherein information is rapidly sent. For example, with respect to a patient, who may have the present invention on or in his or her body, when a reader is used to access information, the information specific to the patient is immediately accessible via a burst download using a capacitor/battery storage device 106 within the hub.

For decoding information using infrared photon techniques, in one exemplary embodiment, strips of different types of heat transmissible material are imbedded in the tag 20. In one embodiment, one strip is a linear bubble of air, which is a poor heat transmitter, and the next is a thin plate of metal, which has higher heat conductivity. When used together as an off/on pattern, the tag 20 is encoded with any type of information needed. For simplicity, a bar code is a preferred embodiment to provide encoded information using this technique.

In another preferred embodiment (not shown), the respective reader is operable to access a national database containing information about a plurality of the present invention. The reader sends the information to the computer containing the national database and processes the information, reads and matches the identification with the specific invention. For example, if the present invention 10 is used on a patient, the information provided is specific to the patient. Likewise, information specific to a container which is secured by the present invention, such as in through a security check point, such as may be used by the United States Customs Department, is also assessable in the same manner. With respect to a patient, examples of information that can be stored in the database, but not limited to, include critical information about the patient as well as name, date of the surgery, and drug allergies.

The length and the width of the invention 10 can be a plurality of sizes, where the length and width are tailored and customized for a given or particular application, such as, with respect to medical uses, any patient ranging from an infant to an adult or even large mammals. For example, when using the present invention 10 as a suture, a smaller embodiment of the present invention could be used for a child when compared to an adult. Specifically, depending upon the thickness of a sternum, bone or fascial wound size, the length can be customized. The thickness of the linkage device 10 in the medical application can also vary from less than a millimeter to a width matching the distance between two adjacent ribs of a given patient, or animal. In the case of a long bone, thicker bands of the linkage device may be preferable.

In a preferred embodiment, when used for medical purposes, the invention 10 further includes an antibiotic and/or antifungal impregnation of the linkage device 10. The present invention may also have a bacteriostatic and/or a bactericidal coating. The antibiotic and/or antifungal impregnation may help to reduce the incidence of postoperative wound infections, and osteomyelitis. The device may be biodegradeable in the body whereas it is designed to last as long as needed to serve its closure purpose. In another medical use (not shown), externally applied inductive power can be supplied to heat the linkage device to coagulate local tissues by heating the linkage device to a defined temperature, such as in tumors of the liver where the device has been deployed by a catheter into the tumor. The device may be designed to fail at a certain temperature, to prevent damaging, such as by boiling, the surrounding tissue.

As illustrated in FIG. 5, in another preferred embodiment, the present invention 10 has a multi-layered strip 12, or an annular ring configuration. In one embodiment, the inner layer 62, consisting of a casing and an inner canal, is an opening that can be placed under vacuum. The next outer layer 64 is a plurality of fiber optic strands. The next layer 66 is a plurality of metal threads, such as a spiral core that may be conductive. The outer layer 68 is a plastic composite. One layer can be a cavity to allow a fluid to be transported through. One skilled in the art will readily recognize that the order of layers are interchangeable and that the combination of layers may be changed to include more or fewer layers than discussed, such as will be discussed below.

In a preferred embodiment, as illustrated in FIGS. 6 and 7, the strip 12 has an air channel 70 disposed within an outer layer and that is vacuum-sealed. The tag 20 has a reservoir 72, such as an inkwell, connected to it wherein ink in the reservoir 72 is under pressure and allows information, or markings, on the tag 20 to be visible. If the present invention is tampered with, the vacuum-seal is broken and the ink exits the reservoir 72, entering into a second reservoir (not shown), or leaving the present invention and getting the ink on the container that it is used to bind, causing the image of information to become less visible, as shown in FIG. 7. Thus by looking at the tag 20, a user can determine if the present invention 10 has been tampered with, or whether the present invention 10 has failed. Though ink is disclosed above, any flowable medium, such as a liquid, gas, and/or a scent in either a liquid, gas, or solid form, may be used in place of ink.

Similarly, though not shown, in another preferred embodiment, the strip 12 has fiber optic strands disposed within the strip where the strands illuminate the tag 20 or information contained on the tag 20. A light source, such as an external source, is provided, as discussed below, to illuminate the strands. If the present invention 10 is tampered with, where one or more strands are broken, the image of information becomes less visible. Just as discussed previously, by looking at the tag 20, a user can determine if the present invention has been tampered with or whether the present invention 10 has failed.

In another preferred embodiment using fiber optic strands, the strands are doped, such as with a metal, so that a unique frequency characteristic is established for each strand. When a plurality of strands is placed within a strip, a unique spectrum of frequency absorption can be read from the linkage strip 10. If the device is tampered with wherein even one strand is broken, the resulting interrogated frequency spectrum will change. A reader device 90, further illustrated in FIG. 8, as discussed below can be used to detect whether the linkage device has failed or has been tampered with.

As further illustrated in FIG. 8, the present invention 10, either on the strip 12, tag 20, or hub 14, also comprises a port 80 to measure a photon level and/or an electrical flux 82, such as conductive reading or resistance reading, of the present invention 10. In another preferred embodiment, an electric input port 84 and/or photon input port 86 are also provided. Thus in operation, when the present invention has the hub 14 connected to its second end 15, a measurement of the photon flux and/or electrical flux is made and recorded. The same readings are then taken later to compare to determine if there has been a decrease or significant change (one beyond the expected statistical variation for a change that is expected due to environmental conditions). Such a change would then suggest that the present invention 10 had failed or had been tampered with. Similarly, an electric charge can be supplied through the electric port and a resistance measurement is read wherein a second charge, of the same value, and reading may be taken at a destination, or while in transport to determine whether the present invention 10 has failed or has been tampered with. As further illustrated in FIG. 8, a reader device 90 is illustrated which is used to take such readings (electrical or photonic), including a bar code reader 92 to read information on the tag 20 if the information is in bar code form. One skilled in the art will recognize that instead of a bar code reader 92, other reader technology, such as disclosed with respect to FIG. 45, may be incorporated depending on the photonic technology used for the tag 20, including computer software that can read the information from a soft copy of the information.

Figure 29:
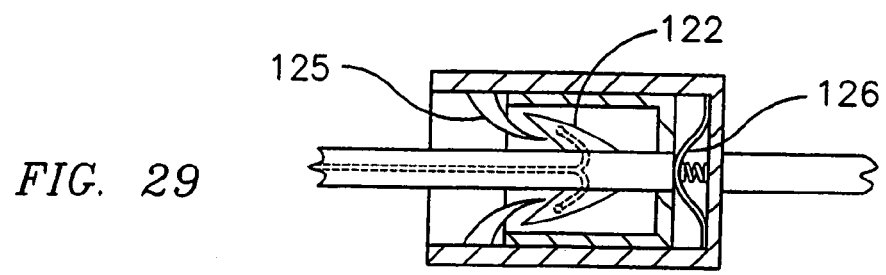
FIG. 29 is an illustration of an exemplary embodiment of the electric socket adapter engaged in a closure hub.

To further illustrate how energy travels through the linkage device, the reader 90 supplies energy, either photonic or electrical, which travels through the strip 12 into the first end 15. As illustrated in FIG. 29, the energy flows through protrusions 122. The energy then travels into the clam feet 125 that make contact with the protrusions 122, therby gaining entrance into the hub 14. Once in the hub 14, the energy is transported by its respective carrier to either a photonic or electrical port.

Figure 9:
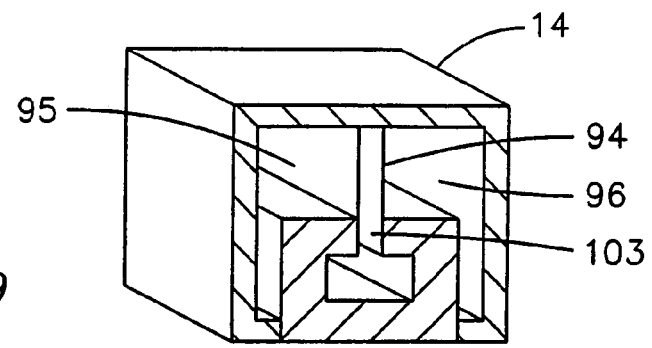
FIG. 9 is an illustration of an exemplary embodiment of a closure hub with a compartmentalized baffle.

In another preferred embodiment, illustrated in FIG. 9, the closure hub 14 has a collapsible baffle 94 disposed within the hub 14 where glue resides. The baffle comprises at least one chamber, but may comprise a plurality of chambers. Once the ends 14, 15 of the present invention 10 engage each other, a user would squeeze the closure hub 14, which in turn causes the baffle 94 to collapse, thus releasing the glue monomers which permanently fixes the ends 14, 15 of the present invention 10 together after the polymeric reaction. In another embodiment, the baffle 94 has two chambers 95, 96 wherein two different reagents are stored and, once squeezed and the reagents combine and go into a slot 103 containing the first end to seal it permanently wherein a polymeric reaction results that seals the ends 14, 15 together. This baffle 94 also may contain material that is released externally to the hub when externally activated. The baffle may contain a medicinal agent.

Figure 10:
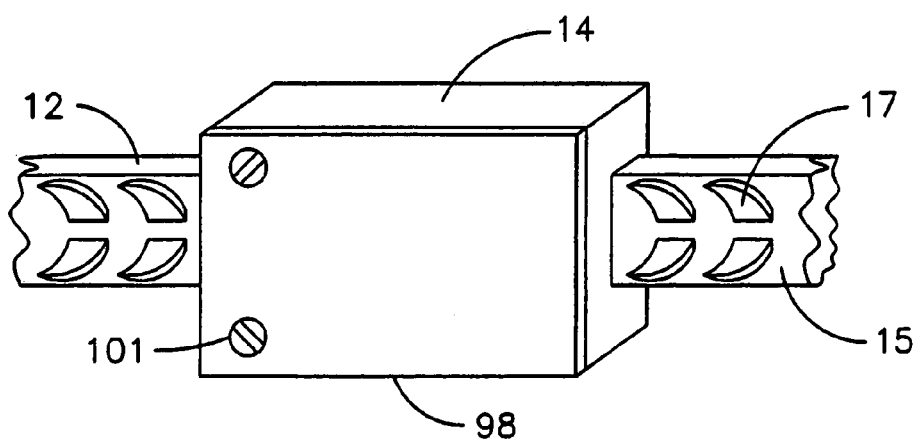
FIG. 10 is an illustration of an exemplary embodiment of a closure hub with a removable top.
Figure 11:
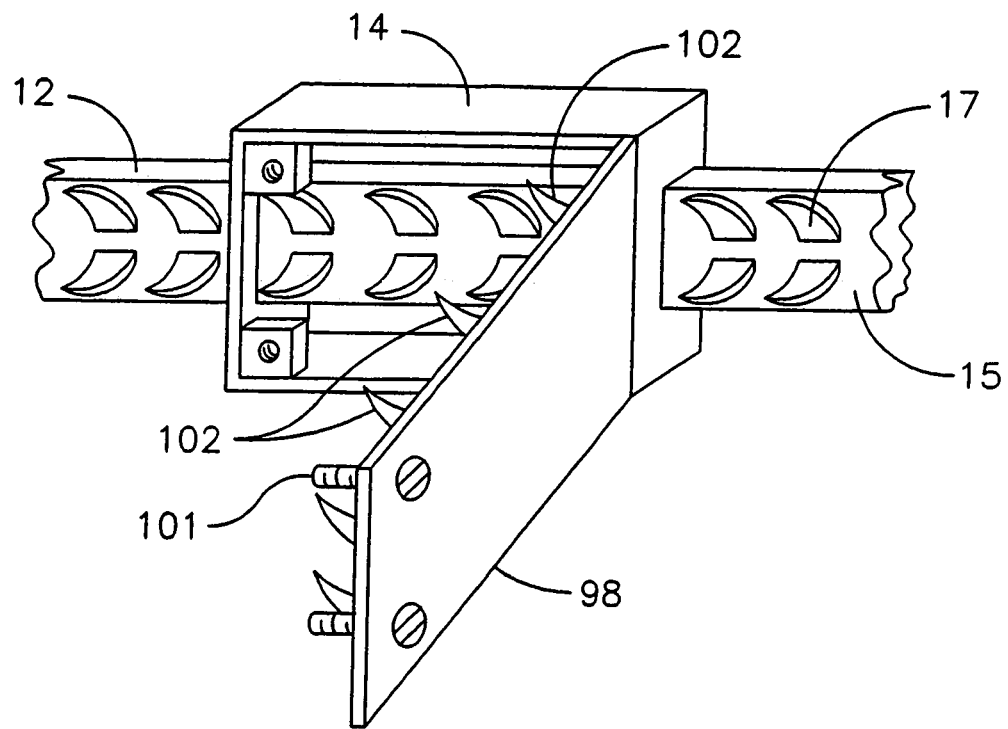
FIG. 11 is an illustration of an exemplary embodiment of the closure hub with the removable top opened.

In another preferred embodiment, the hub device is configured so that the present invention 10 is reusable. In one embodiment, illustrated in FIGS. 10 and 11, the closure hub 14 has a removable cover 98 where screws 101, or another securing component, are removed to open the hub 14. As previously disclosed, the locking mechanism 102 disposed under the removable cover 98 is operable to allow the strip 12 to enter the closure device 14 in one direction but not to exit in the same direction entered. With the cover 98 removed, a user can disengage the end 15 of the present invention engaging the closure hub 14, as disclosed in FIG. 11. In one embodiment the teeth 102 are connected to the back side of the cover 98 so that removing the cover 98 disengages the teeth 102 from the strip, thereby freeing the strip 12 from the hub 14. Though not shown, in another preferred embodiment a single button operates as a release mechanism, releasing the strip 12 from the hub 14

Figure 12:
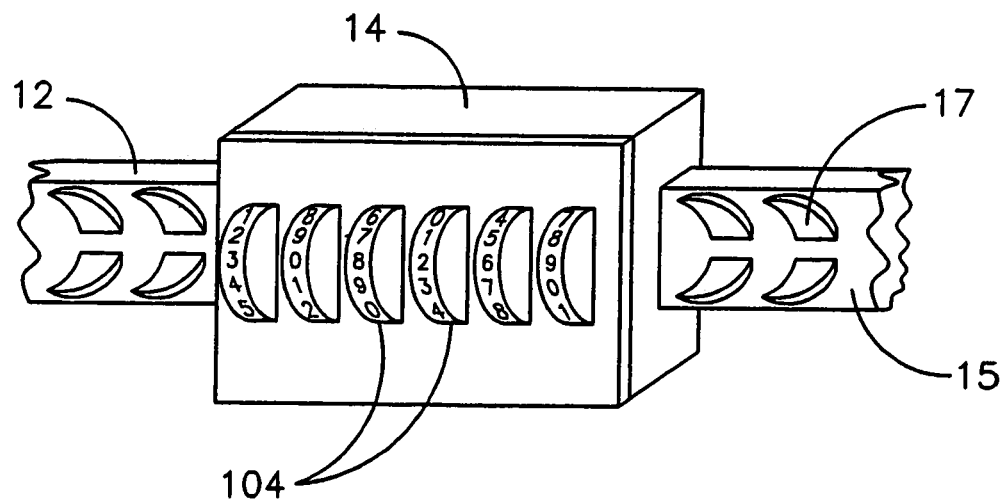
FIG. 12 is an illustration of an exemplary embodiment of a closure hub comprising a combination lock system.

In another preferred embodiment, a control (not shown) within the closure hub 14 is accessible to allow the components 102 engaging the protrusions 17 to release the protrusions only after the cover 98 is removed. In another preferred embodiment, disclosed in FIG. 12, the closure hub 14 has a combination-locking device 104 built into the closure hub 14. When a correct combination is entered, the closure hub 14 releases the protrusions 17 from the hub lock. In another preferred embodiment, the closure hub 14 releases the second end 15 when a passive tag is passed near the present invention, which in turn activates the closure hub to release the second end.

Figure 44:
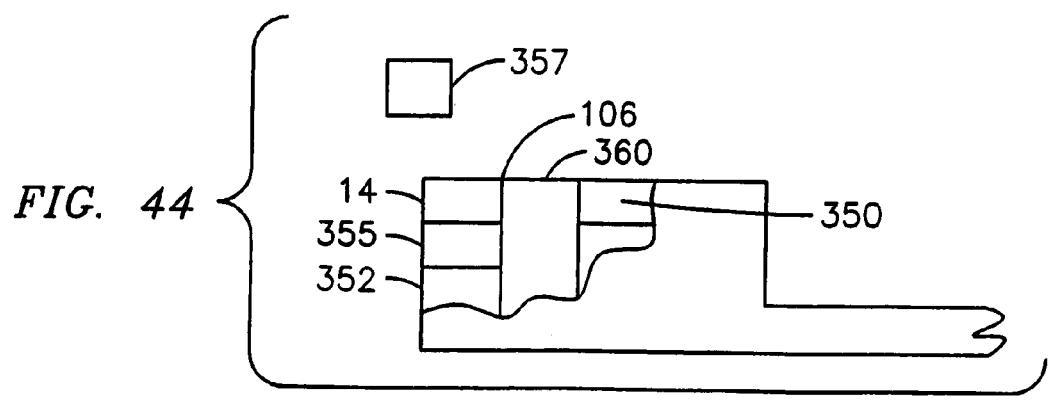
FIG. 44 is an illustration of an exemplary embodiment of a block diagram of a passive detection system for a linkage device.

In another preferred embodiment (not shown) the present invention has an electronic chip that releases the closure hub 14 from the second end 15 when an electrical code is recognized by the chip. The electrical code can be generated by a device generating the electrical code and included in a plurality of objects, such as a key chain. In yet another embodiment, illustrated in FIG. 44, passive identification technology is used to release the strip 12 from the hub 14 wherein when a passive tag is passed near the linkage device 10, the hub 14 will release the strip 12. More specifically, the hub 14 has an electronic latch system 350 which releases the strip 12 when a proper signal is recognized. The hub 14 is electrically activated with a circuit 352 that moves the latch 350 between a first (closed) and second (open) position. A portable power supply 106 is also provided. A power signal transmitter 355 is connected to the power supply 106 for transmitting an inducing power signal at a predetermined electromagnetic flux. A passive identification tag 357 is attached to a device, such as a key chain, and is preprogrammed with an identification code that is pre-selected from a large number of available identification codes. The passive identification tag 357 is responsive to the power signal and provides a return signal on the power signal representative of the preprogrammed identification code so that the power signal acts as a carrier of the imposed code signal. A reader circuit 360 is connected to the power signal transmitter and to the electrical activation circuit. The reader circuit 360 is responsive to the return signal to activate the electrical activation circuit to provide power from the portable power supply to move the latch between the first position to the second position, when the reader circuit determines that the identification code represented in the return signal matches an authorization code stored in the reader circuit 360.

Figure 13:
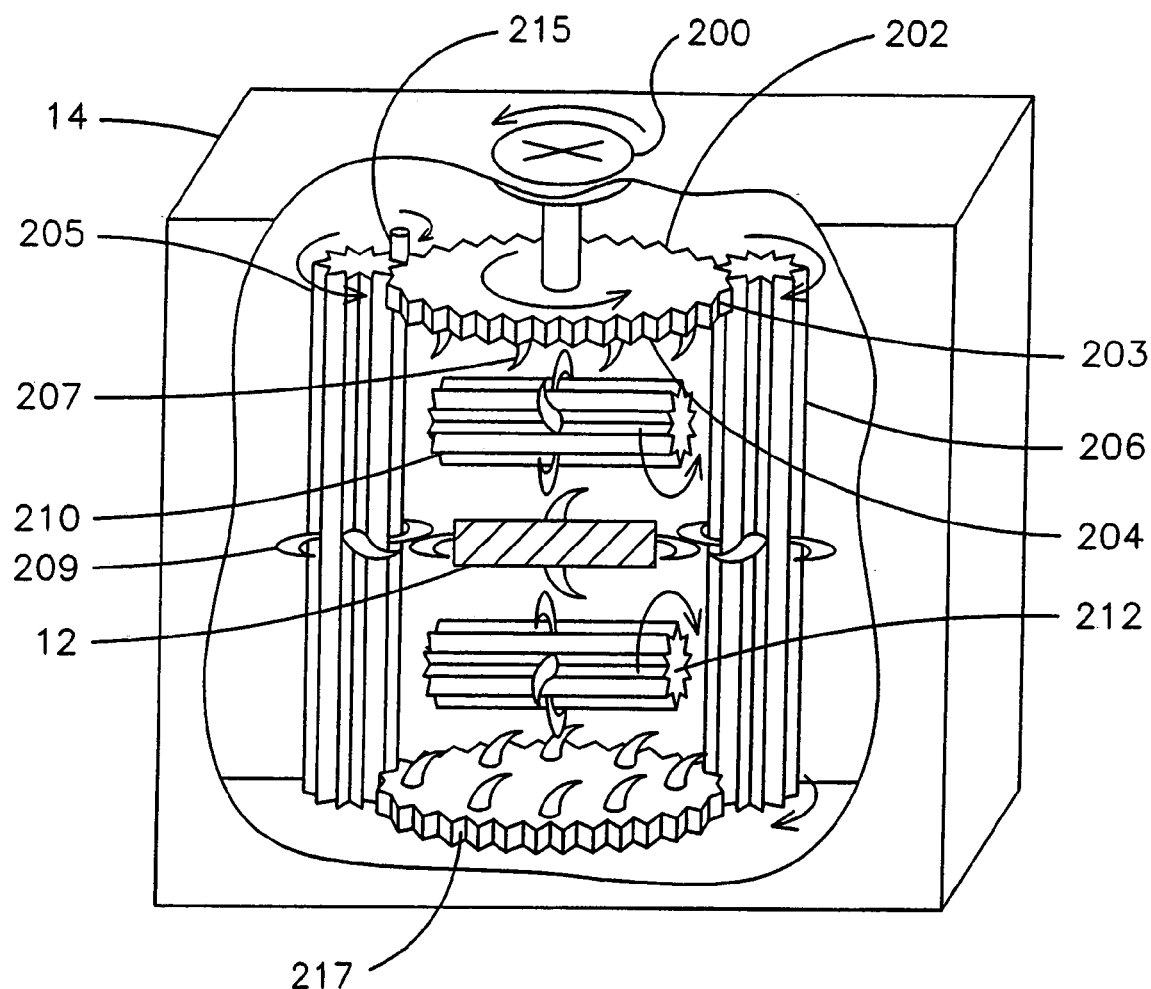
FIG. 13 is an illustration of an exemplary embodiment of a torque screw securing and releasing system.

In another preferred embodiment, illustrated in FIG. 13, an adjustable torque screw is disclosed as part of the hub 14. One skilled in the art will readily recognize a plurality of ways that an adjustable torque screw can be mechanized as part of the hub 14. FIG. 13 illustrates one embodiment where the torque screw 200, when rotated is used to either feed the strip 12 into the hub 14 or to remove the strip 12 from the hub 14. In a preferred embodiment as illustrated, the torque screw 200 is connected to a flat ratchet wheel 202 that has an outer edge 203 that engage rollers 206, 215 where the second roller 215 is a reverse roller engaging a second vertical roller 205, causes it to turn opposite the first vertical roller 206. The bottom of the plate 204 has protrusions 207 that engage a horizontal roller 210. The vertical and horizontal rollers 205, 210 engage the strip 12. Beneath the strip 12 is a second horizontal roller 212. A reverse roller 215 is provided between the right vertical roller 205 and the ratchet wheel 202 which allows the right vertical roller 205 to spin in the opposite direction of the left vertical roller 206. Torque screw 200 turns the ratchet wheel 202 to the right (or left) which engages the vertical roller 206 and turns it in a counter direction left (or right). The reverse roller 215 on the other side engages the ratchet wheel 202 and also turns in a counter direction left. This reverse roller 215 engages the vertical roller 205 to turn it to the right (left). Thus both vertical rollers 205, 206 spin in opposite directions to pull/push the strip 12 into/out of the hub 14, via their directional influence on the turning of the horizontal spikes 209 and due to the turning of the bottom ratchet wheel 217 by the vertical roller 205, while the top ratchet wheel 202 is turned in an opposite direction by the torque screw 200.

Figure 14:
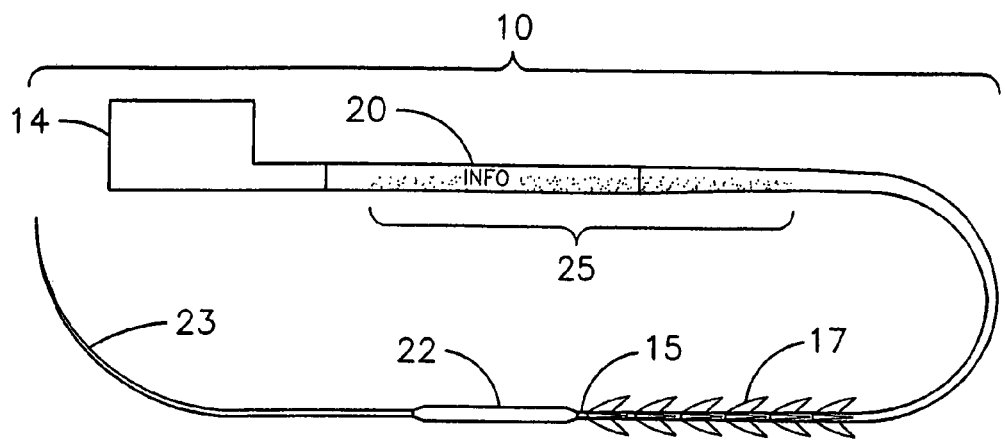
FIG. 14 is an illustration of an exemplary embodiment of the linkage device connected to a dilator.

There are numerous medical and dental uses for a preferred embodiment of the present invention. One such use is as a sternum suture-closing device, as is illustrated in FIG. 14. Prior to placing the invention 10 around a sternum, a dilator 22, made of plastic, metal, silk, or Teflon™, secures a needle 23, typically a stainless steel needle, to the second end 15 of the present invention. The invention is made of an X-ray transparent material, and has a closure device hub or socket 14, such as a closure clip at a second end. In a preferred embodiment, shark-tooth ridges 17, or other shaped ridges such as in a recessed double ridge back configuration, begin at the first end 15 and extend for a specified length of the invention 10. On a flat surface between the closure clip, or hub 14, and the ridges 17, an identification plate, tag, or chip 20 is attached, or imbedded. In another preferred embodiment the chip is the hub 14. On that portion of the invention that contacts the anterior aspect of the sternum, an anti-slip surface 25, such as, but not limited to, roughening the backside, or Gortex™, may be applied. This surface will help hold the invention 10 in place as it is wrapped around the sternum and the first end 15 is secured in the hub 14. In another preferred embodiment, the backside may have a glue surface, which will hold the invention in place once stationary for a given period. As already discussed and illustrated in FIG. 4, viper-teeth 19 extend from or near the hub 14 towards the bone being repaired. Similarly, in another preferred embodiment (not shown), reverse viper-teeth 19 are positioned on the hub 14 and extend towards the cavity of the hub 14 receiving the second end 15, thus also assisting in holding the second end 15 in place once inserted into the hub 14.

Figure 15:
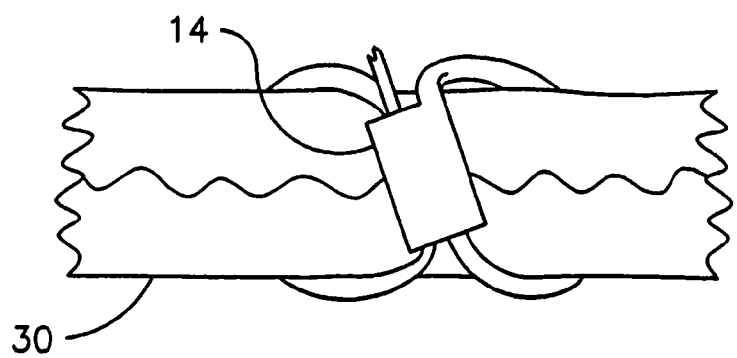
FIG. 15 is an illustration of an exemplary embodiment of another embodiment of the linkage device placed around two bone segments, such as two sternal segments.

In one preferred embodiment, as further illustrated in FIG. 4, once the needle 23 is inserted around the under surface of the sternum 30, or another bone or object, the needle is threaded through the closure clip 14 until the second end 15 of the invention 10 engages the closure hub 14. Then the second end 15 is pulled through until the invention 10 has pulled the sternum 30 together to effect the healing process. FIG. 15 illustrates another configuration of the present invention 10. Instead of being looped around the sternum 30 once, to provide external compression to assist the healing process and to reduce the number of sutures required to close the sternum, the present invention 10 is double-looped, in a "pretzel shape," around the sternum 30. Thus, in this configuration, a single suture closes two sternal segments.

Figure 16A:
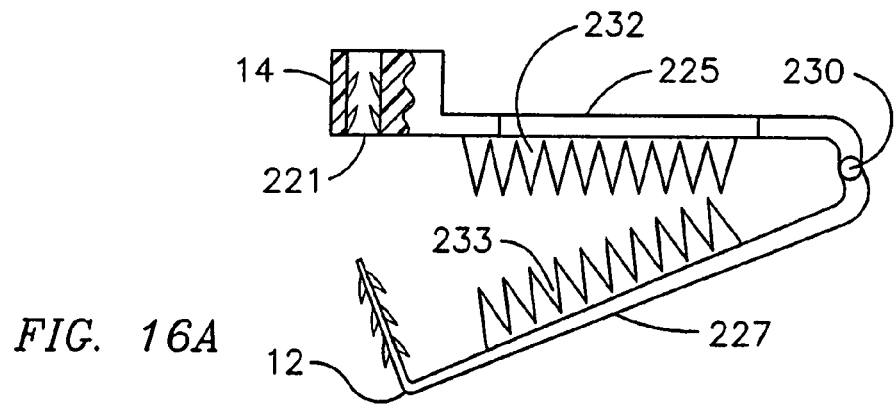
FIG. 16A is an illustration of an exemplary embodiment of a vascular clip with a soft closure mechanism.
Figure 16B:
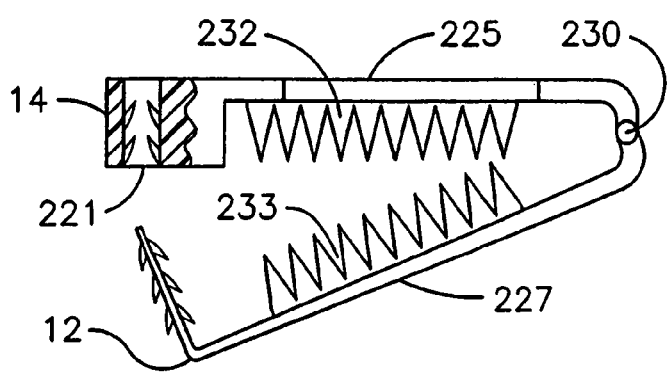
FIG. 16B is an illustration of another exemplary embodiment of a vascular clip with a soft closure mechanism.
Figure 16C:
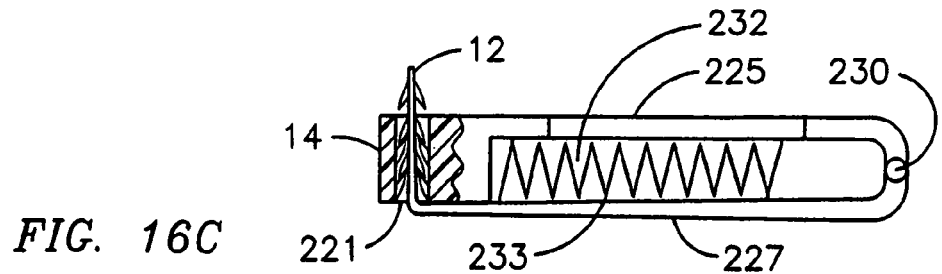
FIG. 16C is an illustration of another exemplary embodiment of a vascular clip, in a closed configuration.

FIGS. 16A, 16B, and 16C are exemplary embodiments of the present invention used as vascular clips. The hub 14 has an opening 221 in a vertical direction wherein the second end of strip 12 bends upward and fits within the opening of the hub 14. The strip 12 has a first part 225 and a second part 227 that are connected by a joint 230. The first and second parts are convexly shaped to apply extra pressure to the vessel or pipe that is being clamped. The first part 225 and the bottom 227 are more rigid. The area where the first part 225 and the second part 227 meet to form the clamp section may have soft or hard teeth 232 and intervening gaps 233 which can be varied in configuration based on the use of the clip. As is further illustrated in FIGS. 16A, 16B, and 16C, in one preferred embodiment the first part has teeth and gaps and the bottom part has alternating gaps and teeth to receive the top half 225 seamlessly when the two parts 225, 227 are approximated at closure as shown in FIG. 16C. These teeth are however soft, and will yield to the vessel, or pipe wall, but will occlude the vessel or pipe lumen. In other preferred embodiment, if needed, the teeth can be hard can act to cut or permeate the structure being clamped.

Figure 17:
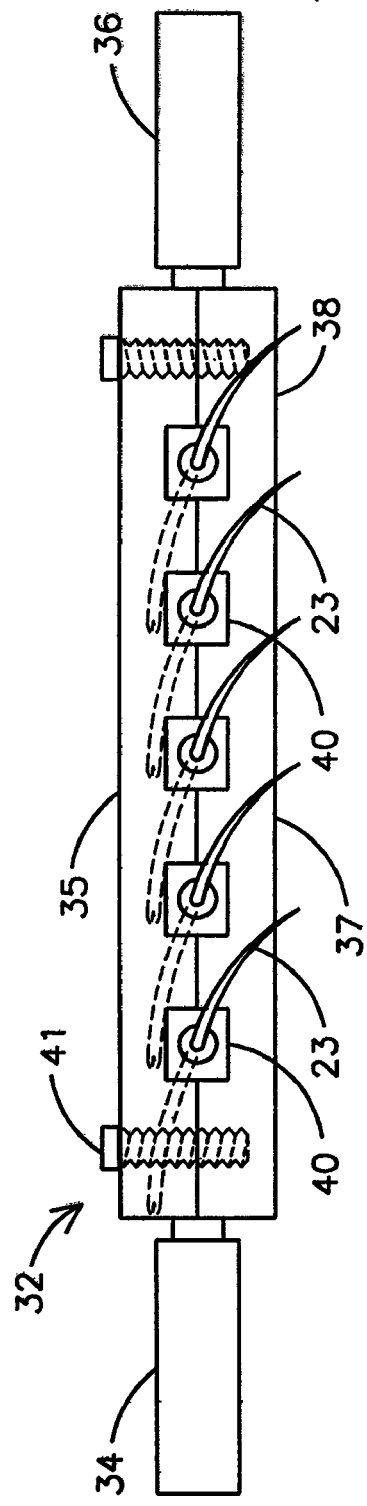
FIG. 17 is an illustration of an exemplary embodiment of an insertion device for long bones and sternal closure allowing for use of a multiplicity of devices for insertion.

A plurality of tools may be used to insert the present invention 10 within a patient. FIG. 17 illustrates a device, an insertion device 32, to allow for a plurality of the present inventions to be placed around a bone or close a wound at one time. As illustrated, the insertion device 32 has a first and a second handle 34, 36. Between the handles is a rod 38, or bar, which has attachments 40 for the needles 23. The needles are attached to each of the present inventions by way of dilators 22, as shown in FIG. 4. In one embodiment, the needles 23 are placed through the rod 38 by separating the rod vertically into two pieces 35, 37 where once the needles 23 are positioned, closure devices 41, such as screws, hold both parts 35, 37 of the rod 38 and the needles 23 in place. One skilled in the art will readily recognize that other embodiments are available to connect the needles to the rod. Since 3 to 6 suture wires are typically used to close a sternum 30, the device can hold as many of the linkage devices as needed. In a preferred embodiment, the needle attachments 40 are adjustable in a right to left direction, or a lateral direction along the rod 38 when the insertion device 32 is parallel to a horizontal surface, so that a spacing of the needles 23 is specific to a given patient. This spacing can be pre-set based on measurements taken from a pre-operative X-ray of rib interspaces of the patient, or made at the time of wound closure, tailored to fit the size needed.

Figure 18:
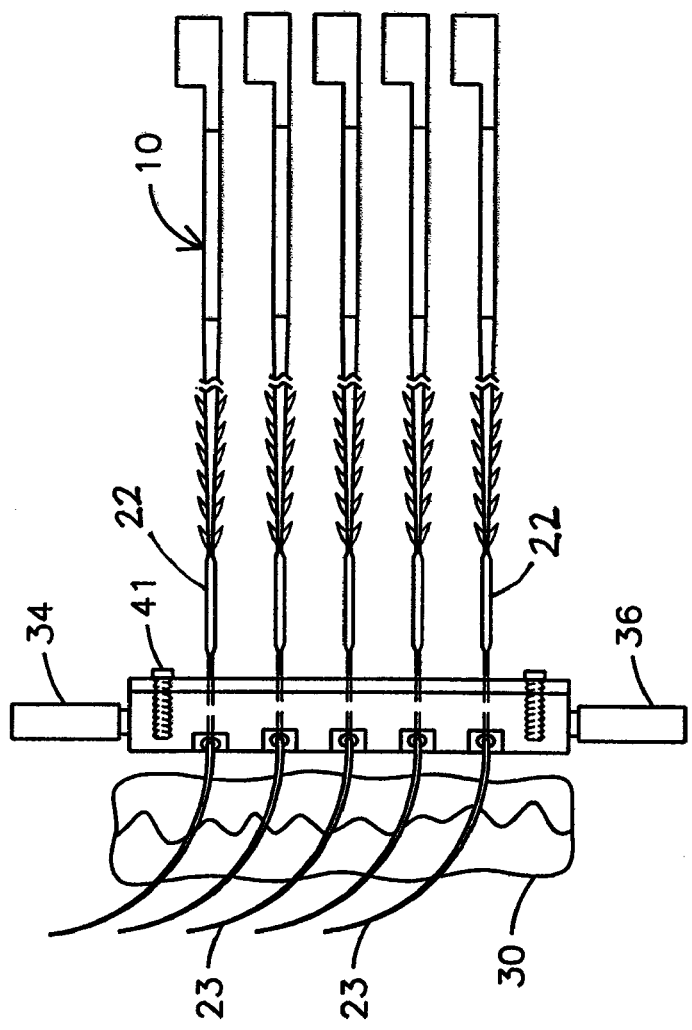
FIG. 18 is an illustration of an exemplary embodiment of an insertion device in use.

In operation, as illustrated in FIG. 18, a surgeon holds both handles 34, 36, similar to holding a rolling pin, while standing on the patient's side, such as the left side, of a patient above the split sternum. The needles 23 are introduced into the intercostal spaces on the side of the sternum farthest away from the surgeon. The handles 34, 36 are physically rotated with a forward twist to insert the needles through the muscle layer. Once through the muscle layer, the device is pulled towards the surgeon advancing the needles behind the sternum 30, until the needles 23 start to protrude through the intercostal interspaces on the other side of the split sternum 30 (i.e., the side closest to the surgeon). The apparatus is unclamped, and then each needle 23 is pulled through the intercostal space, such as with forceps. Each needle is then threaded through the hub 14 of the linkage device 10 to secure the invention around the wound, split sternum or any other defect requiring closure. For example, an osteoporotic femur 42, as illustrated in FIG. 19, fractured in multiple places requiring an intra medullary rod 44 and multiple circumferential support bands 10 to hold the bone together. As is discussed in more detail below, in another preferred embodiment of the linkage device illustrated in FIG. 19, a single hub 145 has a plurality of strips 12 extending from the hub 145. The hub 145 has a plurality of openings to accept the plurality of strips 12. As further illustrated in FIG. 19, the linkage device having the plurality of strips can be used for certain areas of a body, such as for fixation of a fractured greater trochanter 47 located on the femur.

Figure 20:
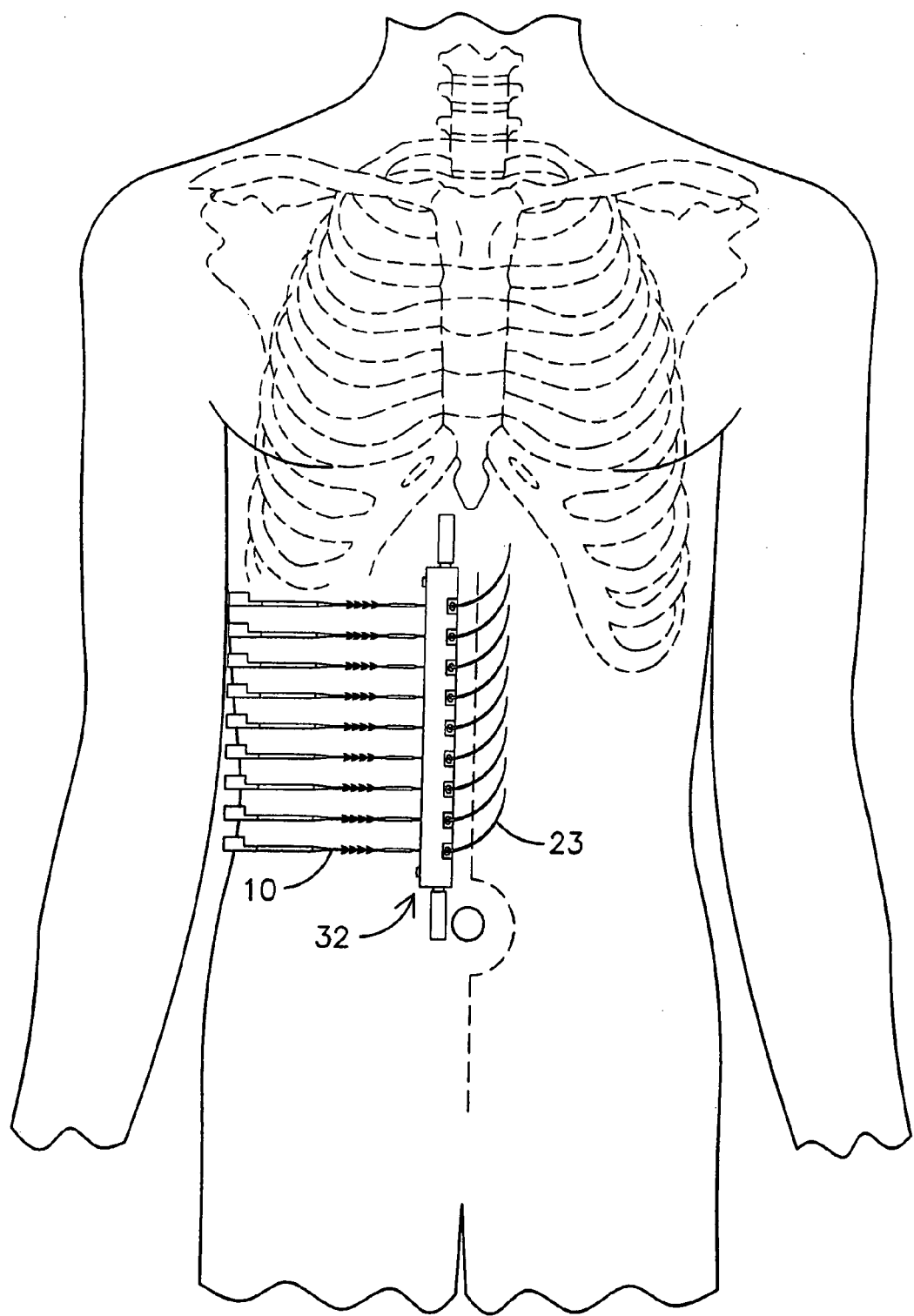
FIG. 20 is an illustration of an exemplary embodiment of the linkage device used to close a long fascial wound.

In another embodiment, the insertion device 32 is used for long fascial wound closures, such as closing an abdominal wound as disclosed in FIG. 20. In larger patients, steel sutures are currently used to close an abdominal wound because of the increased tensile strength of the wire versus routine silk and catgut dissolvable suture material. In a preferred embodiment, the insertion device 32 is expandable to close a long wound, such as a long abdominal to pelvis incision. For such an incision, the insertion device 32 is expanded up to, but not limited to, 40 to 50 cm.

Figure 23:
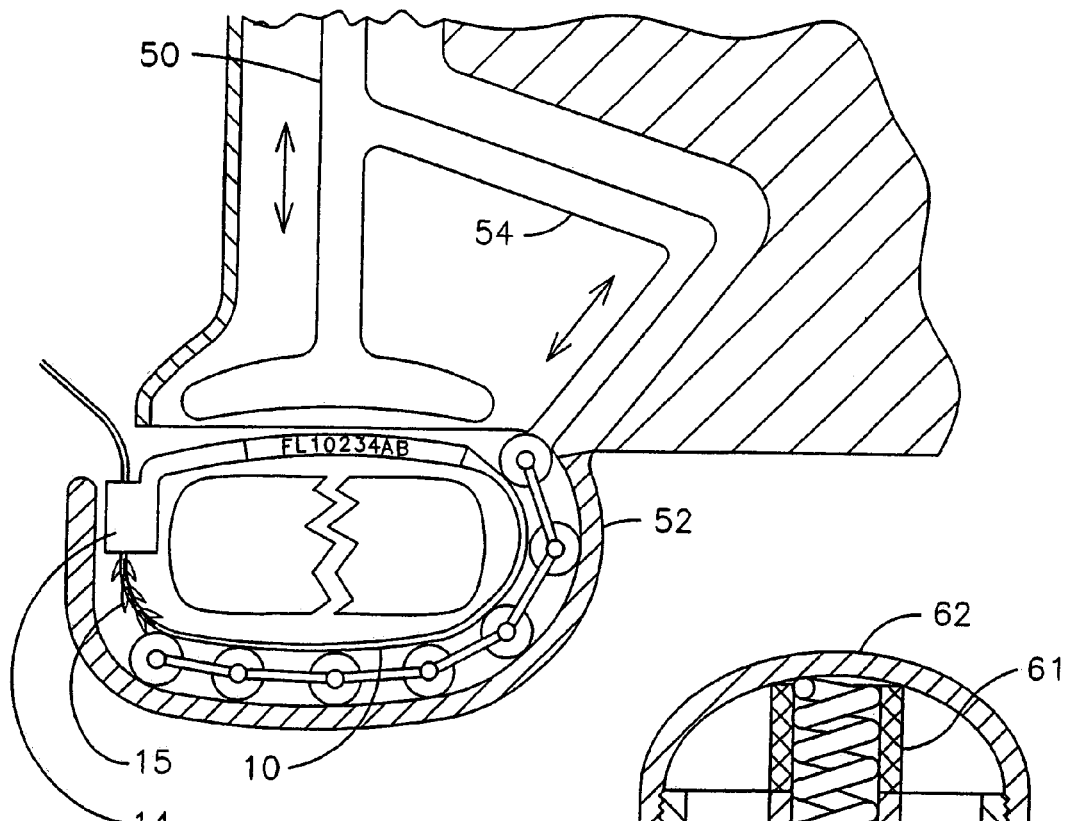
FIG. 23 is an illustration of an exemplary embodiment of an insertion device with a stamper.

In another preferred embodiment, a crimper/staple-like apparatus 46, or gun, is used to secure the linkage device around a bone 30. In a preferred embodiment, disclosed in FIG. 21, the gun has crimper jaws 48 that bend the ends backward, as disclosed in FIGS. 21 and 22, and then when activated, push the linkage device 10 around the bone causing the ends 14, 15 to connect and lock. FIG. 22 further illustrates a plurality of closure devices 10 loaded internally within the insertion gun 46. A spring-loaded handle 49 is pulled close to activate closure of the crimpers 48. In another preferred embodiment, illustrated in FIG. 23, the stapler device has a stamper mechanism 50 and a guide device 52 that fits around the bone, or object, being mended, and comprises a push-arm mechanism and roller device 54 to assist in placing the linkage device 10 and smoothing it out to insure a secure fit around the bone and assists in locking the ends, 14, 15 together. The stamper mechanism also has the ability to imprint a date, time, or other information impression upon the linkage device where the imprinted information can be read (e.g., physically photonically, or electronically).

Figure 24:
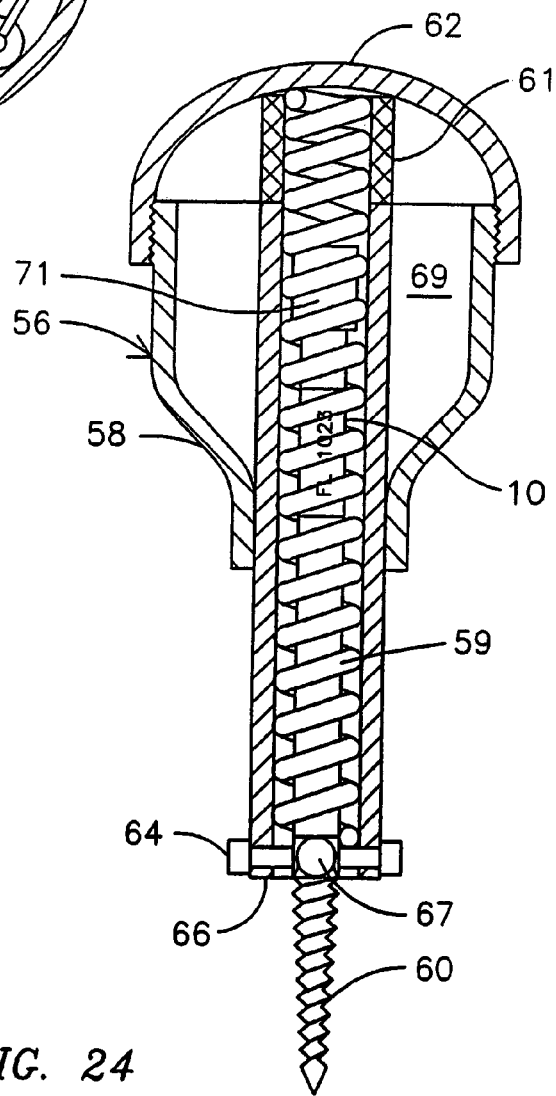
FIG. 24 is an illustration of an exemplary embodiment of a drill insertion device.

In another preferred embodiment, illustrated in FIG. 24, a drill bit apparatus 56 is used to insert the linkage device 10 into a hardened substance, such as a bone and/or concrete. The drill bit apparatus 56 could be used in a surgical procedure involving Stealth Technology™, such as with a reference frame used to repair a fractured knee or damaged ligament. As further illustrated in FIG. 24, the apparatus 56 has a main body 58 and a drill bit end 60. A cavity 69 in which the linkage device 10 fits is located within the main body 58 of the apparatus. In one embodiment, a top end 62 of the main body is removable so that the linkage device 10 may be placed within the cavity 69. The drill end 60 is detachable from the main body 58, such as by way of detachable clamps 64. Thus, in a second embodiment, the drill end 60 is removed from the linkage device 10 by a screw 67 attaching the two. The device is then placed into the cavity through a second end 66 of the main body 58, which is an alternate loading method.

In operation, either the whole apparatus 56 is rotated to allow the bit 60 to burrow into the hardened substance or in a preferred embodiment, the main body 58 has a spring 59 which allows the apparatus to be spring activated and turned by pushing up and down by hand on the main body 58 where a compression wall 61 is provided around the spring. Those skilled in the art will recognize other ways in which to mechanize the apparatus 56 so as to effectuate a spring loaded drill press.

Figure 25:
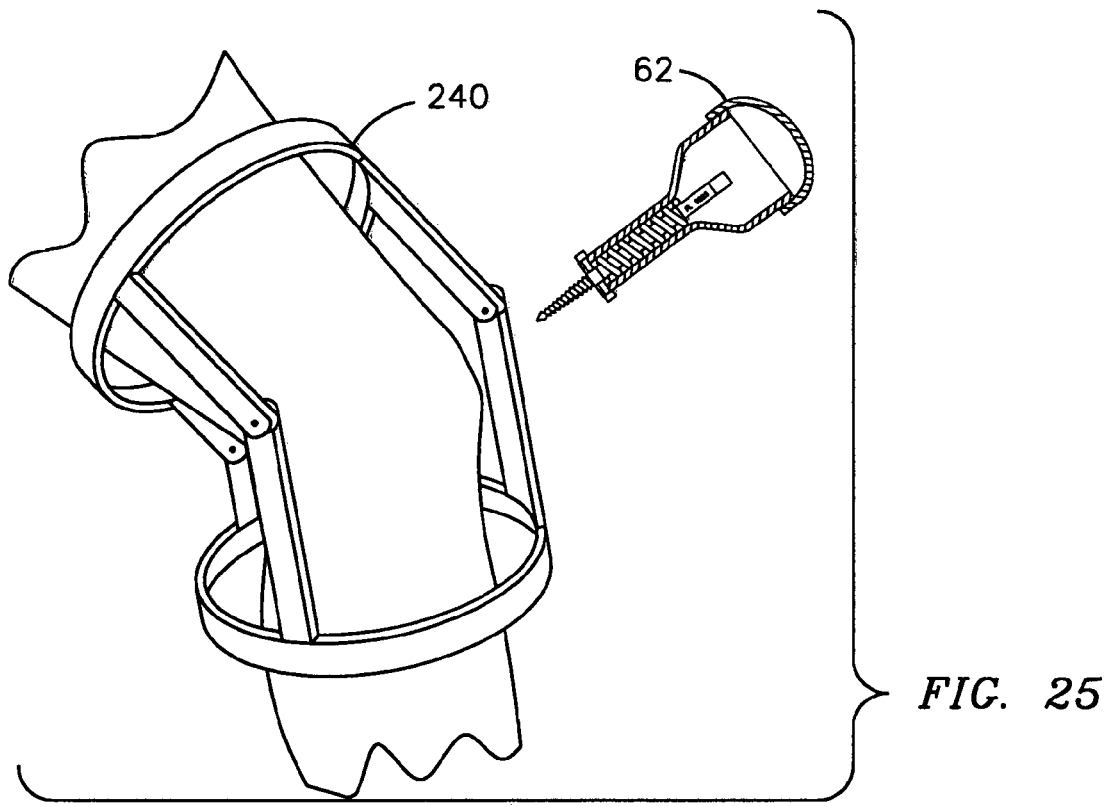
FIG. 25 is an illustration of an exemplary embodiment of a drill insertion device used with Stealth Technology™.

In another embodiment an electric motor or air powered driving device 71 within the apparatus 56 turns the bit end 60. Though not illustrated, if the device is rotated, either a motor or an air powered rotation device is provided. In another preferred embodiment, the connection 67 between the drill end 60 and the main body 58 is configured to allow the drill end 60 to pivot up to a one hundred and eighty degrees about the connection point 67. In another embodiment, such as when used with a Reference Frame 240, this device and its insertion can be coordinated with the patient's own unique anatomy determined from either a prior CT or MRI study. Stealth Technology™ has used this type of information in spinal surgeries. As is further illustrated in FIG. 25, the tip can be robotically guided and/or includes technology to be autofinding to locate where to insert the linkage device 10 within a body of material. Infrared or other locator diodes help to reference the apparatus 56 to the patient in the Stealth™ Reference Frame 240.

Figure 26:
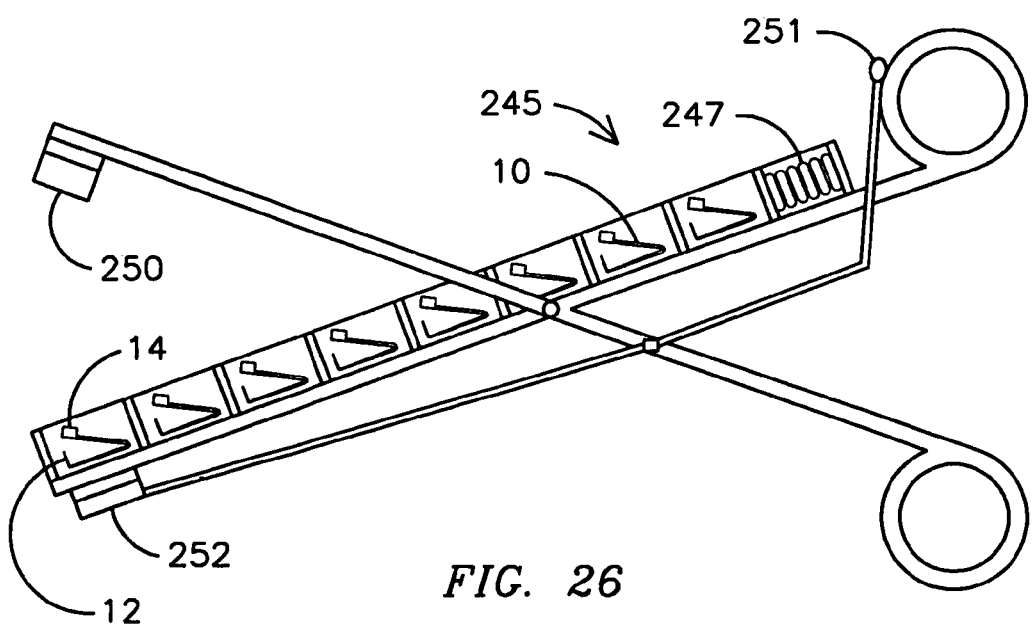
FIG. 26 is an illustration of an exemplary embodiment of an insertion device for a plurality of vascular clips.

With respect to the vascular clip multiple insertion device configurations, a preferred embodiment of an insertion device is illustrated in FIG. 26. The insertion device 245 holds a plurality of clips, or linkage devices 10 where when one is inserted, a spring 247 pushes another clip 10, as illustrated in FIGS. 16A and 16B, into place for insertion. As illustrated the insertion device 245 has an area 250 to close the clip 10 about to be inserted and an insertion hammer 252 that pushes the clip into the operative field and then together presses the end of the strip 12 into the hub 14. A second arm 251 is provided on the insertion device with a hammer end 252 that pushes the clip 10 out of its resting place and into the surgical field.

In another preferred embodiment, the linkage device may be daisy-chained with other embodiments of the linkage device. Daisy-chaining the linkage devices may be needed to fit the linkage devices around an object larger than the embodiments of an individual linkage device 10 currently at hand. In another embodiment, the linkage devices may be daisy-chained to tether objects or to move objects 110 about a fixed point or object 112, as disclosed in FIG. 27. In such cases, a need may arise to provide electrical power through the linkage device, by way of an electrical line imbedded within the strip 114. In a preferred embodiment, illustrated in FIGS. 28 and 29, a power feeder 120, or electric socket adapter, fits within a closure hub 14. The power feeder 120 has electric contacts 122 that engage a connection 125 within the closure hub 14, such as "clam foot" contacts 125 extending from the inner surface of the closure hub, to receive the electricity. In a preferred embodiment, a surface within the closure hub 126, which may be spring loaded, is provided to insure that the power feeder 122 contacts make contact with the connection part, or "clam foot," 125 of the closure hub 14. A second end 130 of the power feeder 120 can be plugged into an electric outlet, or connected to some other power source, such as a battery, as further illustrated in FIG. 28. Except for the contacts 122 and connection surfaces 125, the rest of the closure hub 14 and feeder 120 are insulated so that a user can handle these components without receiving an electrical shock. In another preferred embodiment (not shown) where fiber optic stands are used, as discussed above, instead of providing power through the feeder 120, the feeder 120 is used to provide photons from a source to the fiber optic strands of the device 10.

In another preferred embodiment further illustrated in FIG. 27, the hub 14 is motorized where once a strip engages the hub, a motor 140 can be activated, either manually, or self activation, allowing the motor in the hub 14 to pull the strip 12 into the hub's opening as far as needed. The motor 140 may be powered by any source such as, but not limited to, a solar cell that provides electricity to the motor, a fuel cell, such as a battery connected to the linkage device, or an electric hub adaptor as discussed above with respect to FIGS. 28 and 29 where instead of having power feeder 120 fitting within a hub 14, the hub is connected directly to the power feeder 120. In one embodiment, the motor 140 can be reversed should the strip 12 need to be removed from the motorized hub 140 or if more length is needed for the strip. FIG. 27 shows five hubs A, B, C, D and a power hub connection (not labled).

Figure 30:
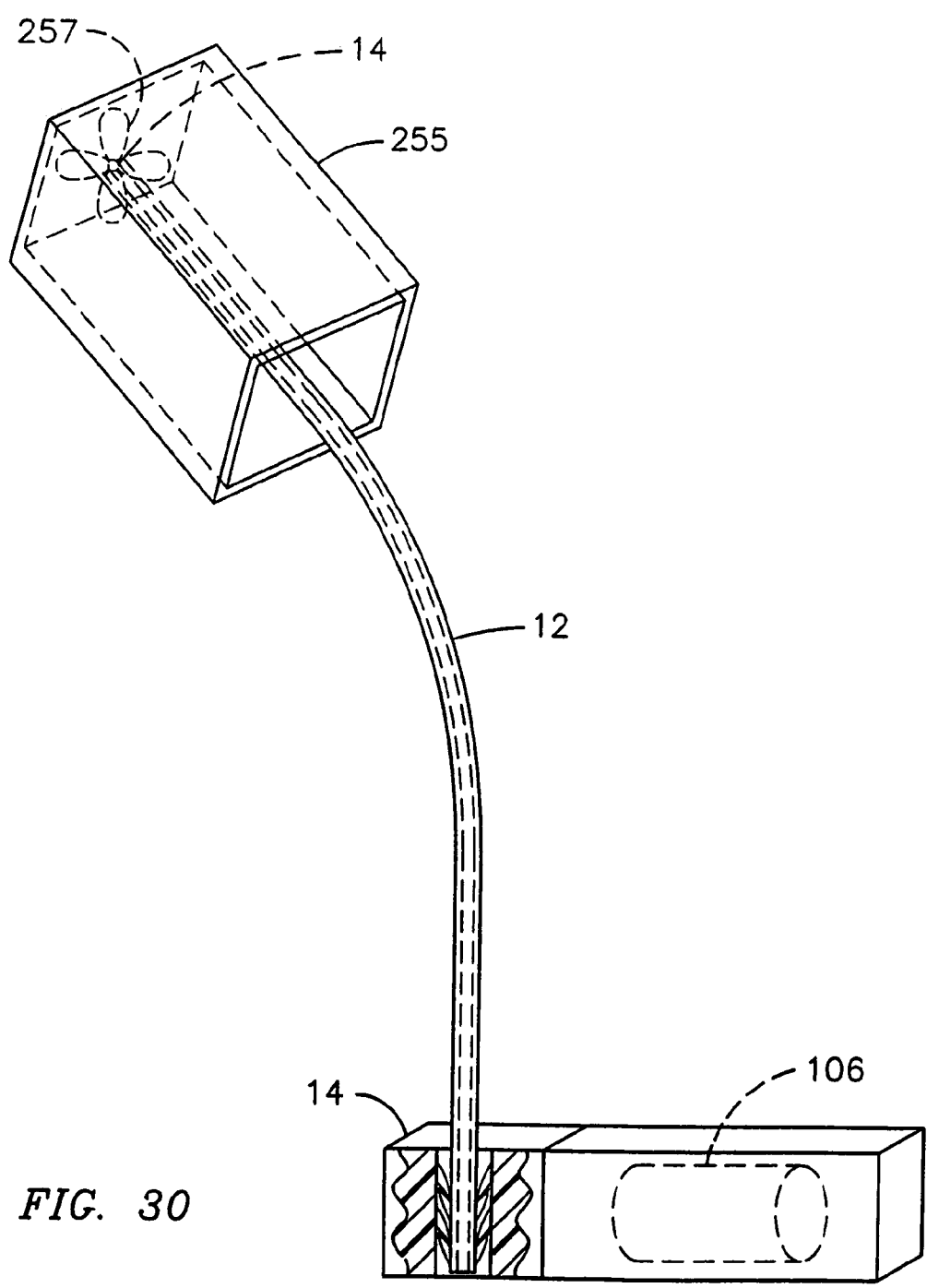
FIG. 30 is an illustration of an exemplary embodiment of a box kite windmill device used to generate power through a linkage device.
Figure 38:
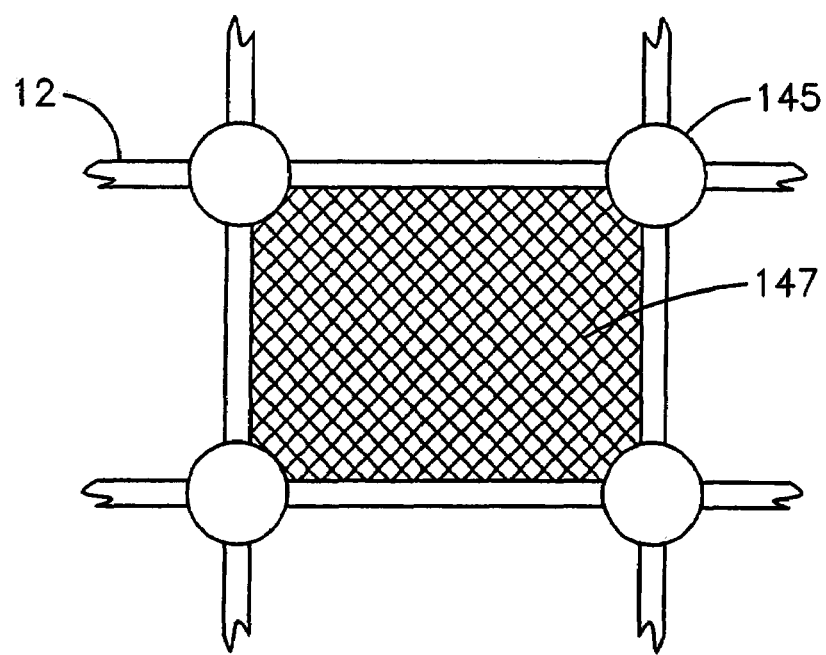
FIG. 38 is an illustration of an exemplary embodiment of a net, fence and/or antenna constructed with a plurality of binding devices.

Power may be generated by or through the linkage device in a plurality of ways. A plurality of power sources 106 can be used. Such power sources include, but are not limited to, battery, photo electric/laser light, inductive power, atomic power, and/or glucose/mitochondrial fuel supply. An example of power being generated is illustrated in FIG. 30. As illustrated, a strip 12 is connected to a kite 255, the sides of which are derived from unspooling, or uncoiling, the devices, as illustrated in FIG. 5A and FIG. 38. The hub 14 has a propeller and generator 257 within it. The turning of the propeller 257, by wind or water, generates electric power which is fed back through the strip 12 to a hub 14, which has a battery storage device 106. The kite itself is composed of interlocking linkage devices where the kite sides are stored within the strip and are spooled out from within the linkage device 10.

In another embodiment power is provided from a remote source 107 wherein the power is then stored in a battery or capacitor, as illustrated in FIG. 2B. Another source of power is inductive power. This can be added to the linkage device wherein power is supplied by connecting the strip to the hub forming a conductive loop that can in turn have current induced within it from an external electromagnetic frequency flux 107.

Figure 31:
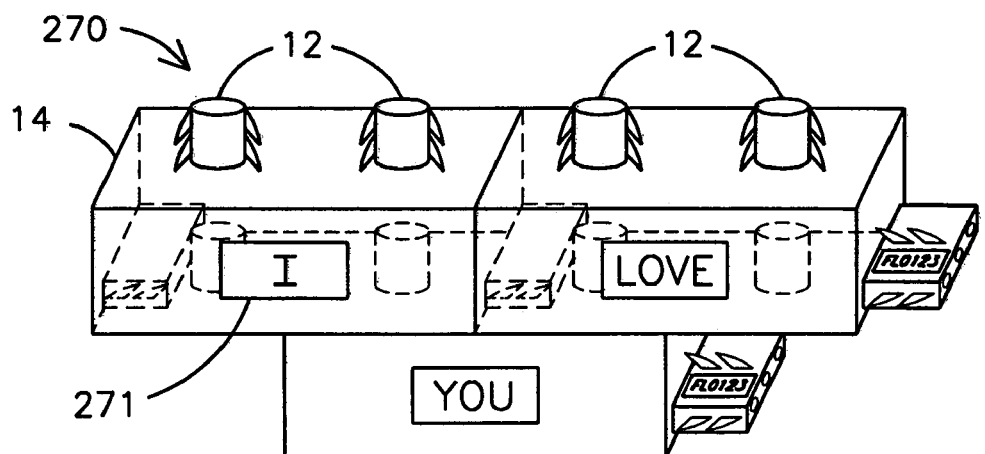
FIG. 31 is an illustration of an exemplary embodiment of a plurality of linkage devices used as a sign.
Figure 32:
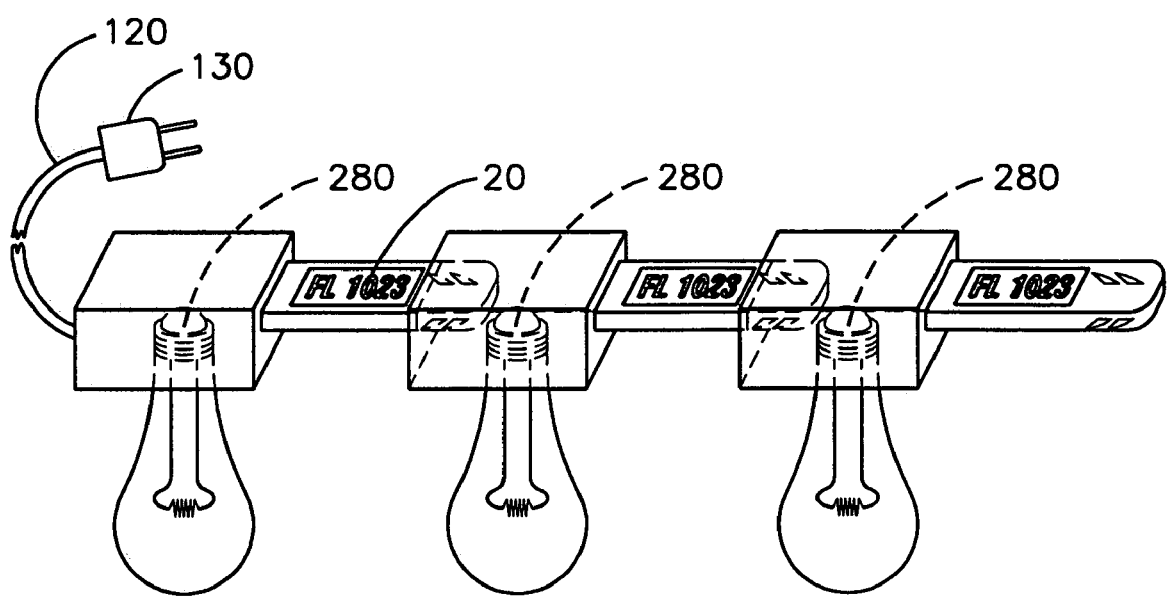
FIG. 32 is an illustration of an exemplary embodiment of a plurality of linkage devices daisy-chained together where the hubs are light sockets.
Figure 33:
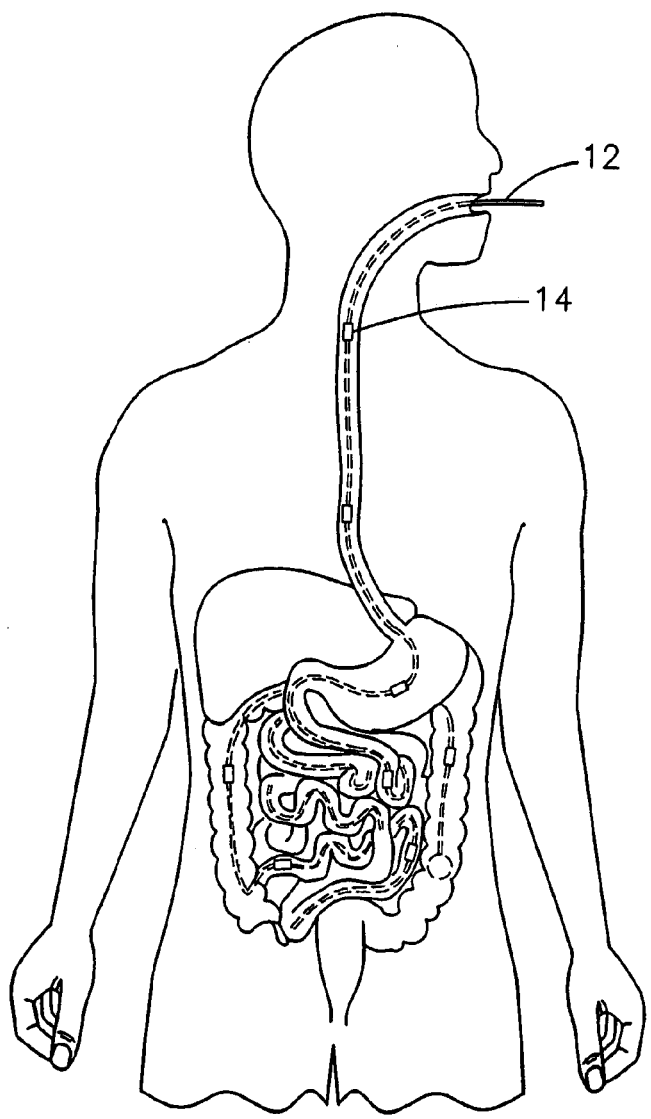
FIG. 33 is an illustration of an exemplary embodiment of a plurality of linkage devices connected and used for an endoscope for the small bowel.

Other embodiments of where the linkage device can be used where it is daisy-chained together and/or stacked are illustrated in FIGS. 31 through 33. In FIG. 31 the linkage devices are used to form a wall sign 270 where the hub 14 has strips, and/or nobs, 12 extending from more than one surface for connection to another hub. A surface 271 of the hub 14 may be used for the signage or display area. FIG. 32 illustrates hubs 14 that have recessed lighting sockets 280, where the identification labels 20 may also be illuminated. Power can be supplied by a plug 130 and wire 120 to the hubs connected in series. FIG. 33 illustrates the linkage device 10 being used as a small bowel endoscope in a human, since the length of the small bowel, approximately twenty-two feet, limits current endoscopes. With the daisy chain ability of this device, as many as are needed can be threaded through the intestines.

Figure 34:
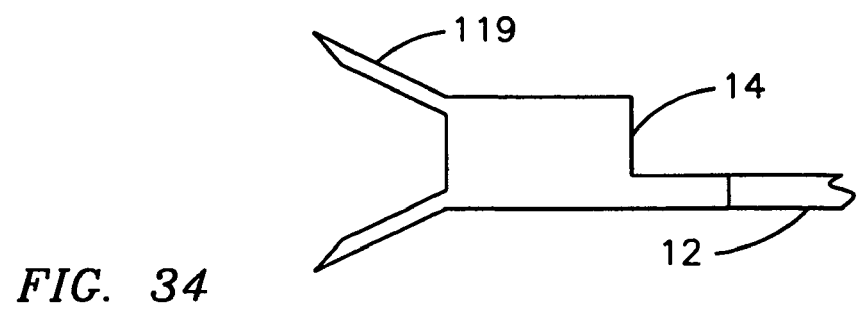
FIG. 34 is an illustration of an exemplary embodiment of a funnel-like device connected to the binding device.
Figure 46:
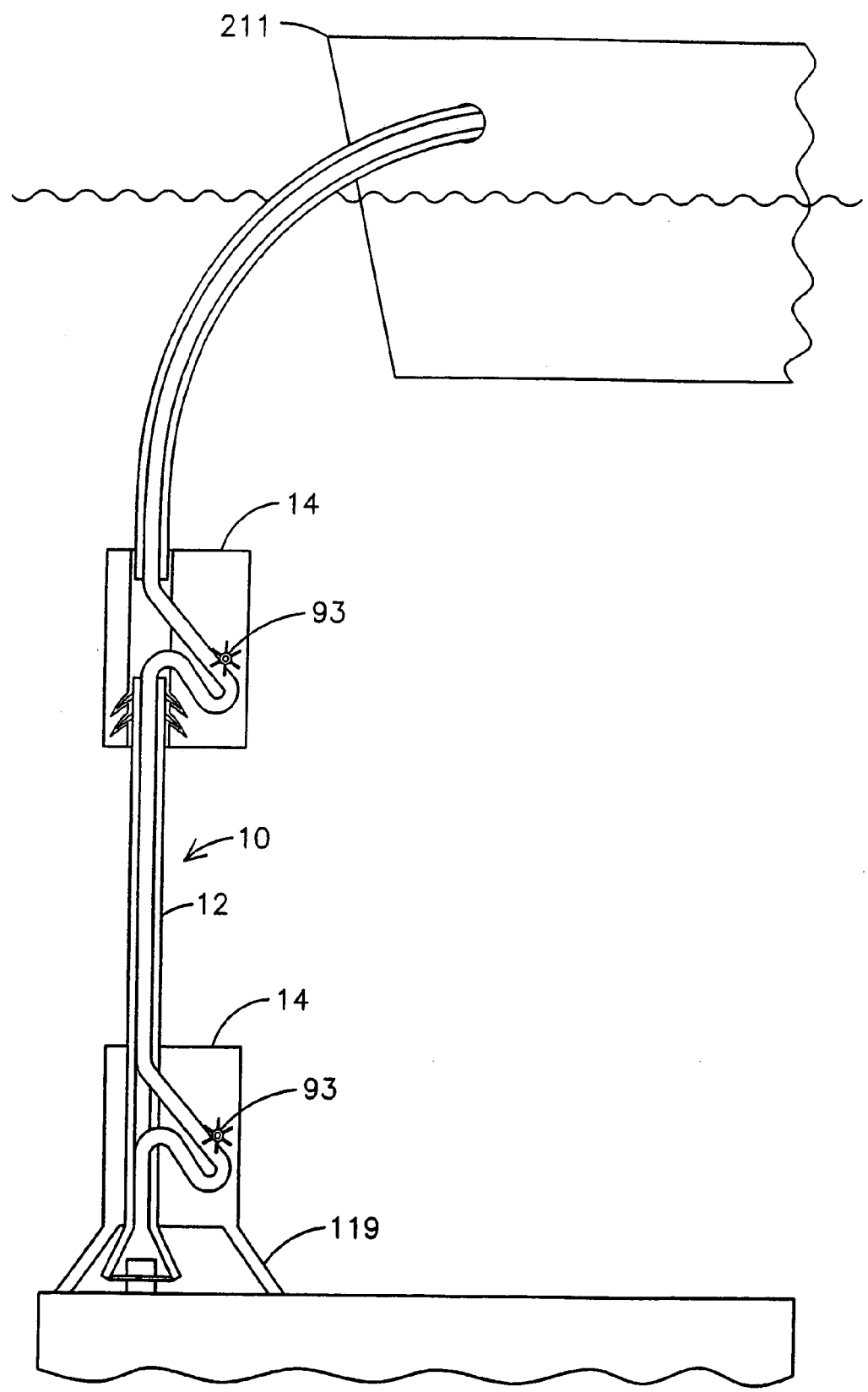
FIG. 46 is an illustration of a plurality of linkage devices being used to pump oil from a submerged oil tanker.

In another embodiment illustrated in FIG. 34, a funnel-like device 119 is connected to the end of the hub 14 receiving the strip 12. The funnel-like device 119 further assists the linkage device 10 in connecting both ends 14, 15 together and can assist in transport of a fluid, including, but not limited to liquid, gas, plasma, and semisolid. FIG. 46 is an illustration of the several linkage devices daisy-chained together and being used to remove a movable medium, such as oil, from a submerged tanker leaking oil. In one preferred embodiment, suction is applied through the linkage devices to pull the fluid through the linkage devices. In another preferred embodiment, illustrated in FIG. 46, the fluid is assisted by paddle devices 93 which are driven by an internal motor powered from an external and/or internal power supply (not shown).

Figure 35:
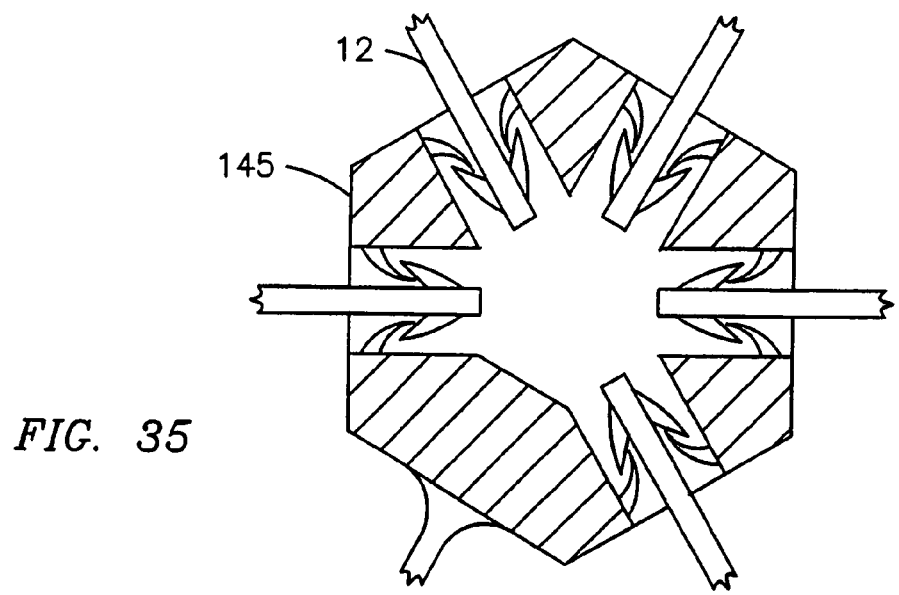
FIG. 35 is an illustration of an exemplary embodiment of a closure hub with a plurality of closure locations.

The linkage device 10 can also be configured where the closing hub, or multi-hub, can accept a plurality of strips within a plurality of openings in a closing hub 145, as illustrated in FIG. 35, as discussed previously with respect to FIG. 19. The hub can have a plurality of different shapes such as, but not limited to, hexagonal, pentagonal, square, or etc., where each side could have an opening disposed therethrough. In one embodiment a single strip 12 is connected to the closure hub 145, but in other embodiments a plurality of strips 12 are connected wherein the number of strips 12 can equal or exceed the number of openings in the closure hub 145. As discussed above, one of the openings may be used to provide electrical power to the linkage device 10, which in turn provides power through all strips connected to the closure hub.

Using a multi-hub, integrated structures can be created, such as a net, or another 3-dimensional structure, wherein a plurality of the linkage devices with the multi-hub 145 are connected to form the basic structure of the net, and a finer material 147 is used to cover the basic structure, as illustrated in FIG. 38. The material 147 is stored, spooled, within a first linkage device, as illustrated in FIG. 5A, wherein the other linkage devices comprise grooves, or connecting surfaces (not shown), to hold the material 147 in place. The material 147 is able to be pulled out and is retractable just like a window shade or projector screen. The center spool 148 is spring-loaded to allow the material to be pulled back inside the outer shell of the strip 12.

Figure 36A:
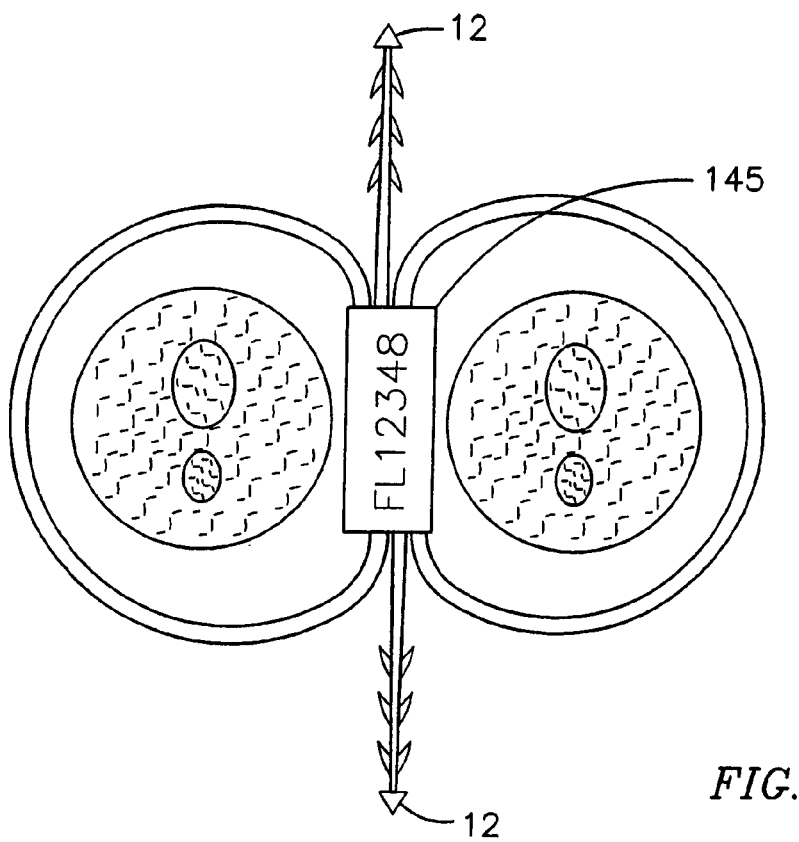
FIG. 36A is an illustration of an exemplary embodiment of a binding device with strips used as handcuffs.
Figure 36B:
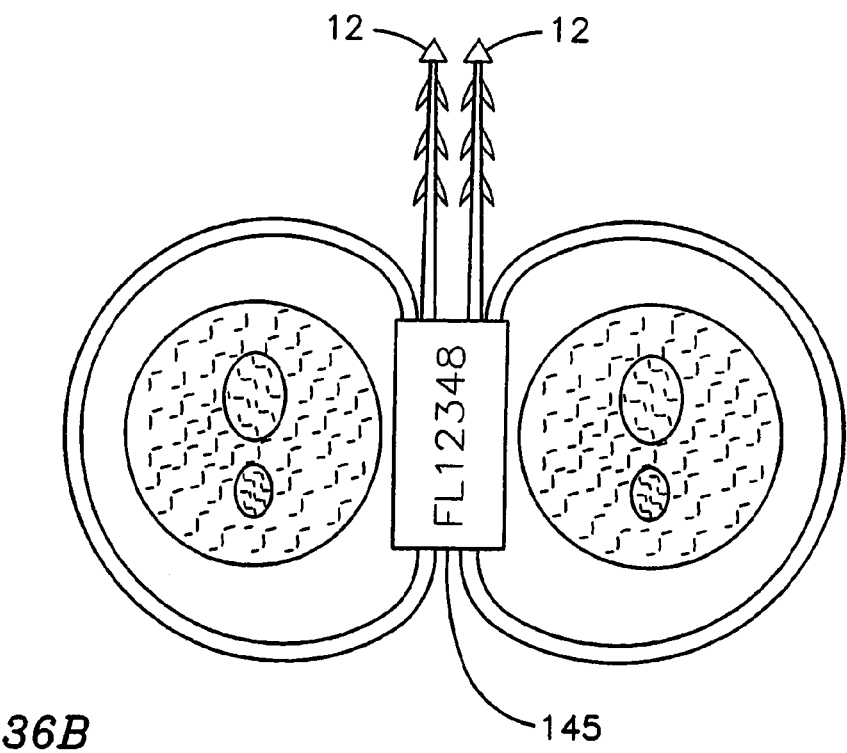
FIG. 36B is an illustration of another exemplary embodiment of a binding device with strips used as handcuffs.
Figure 37:
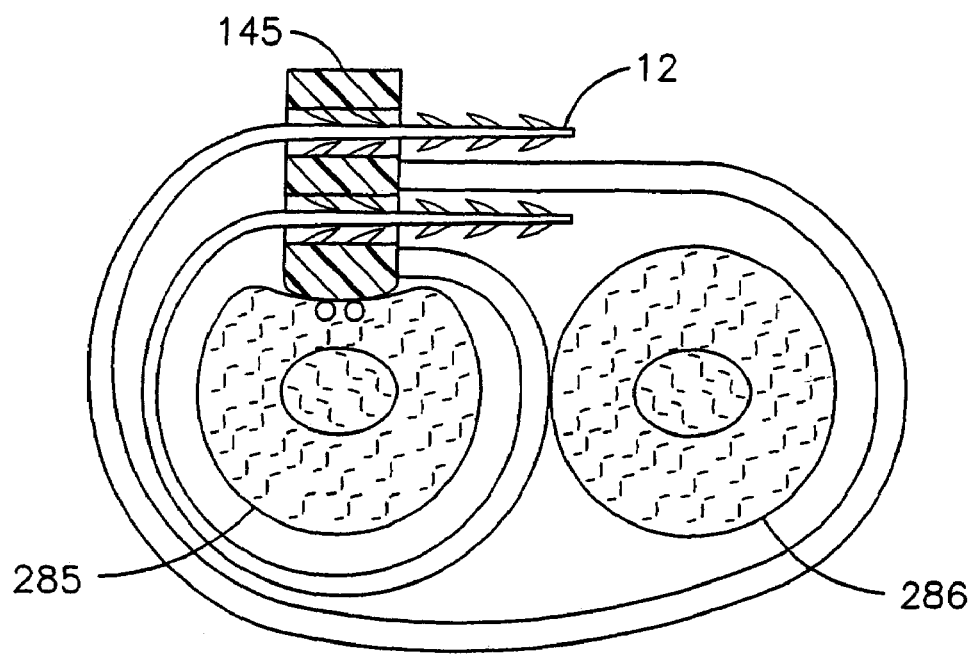
FIG. 37 is an illustration of an exemplary embodiment of a binding device with a two strips in use.

In other exemplary embodiments, such as illustrated in FIGS. 36A and 36B, the linkage device can be used as handcuffs where a multi hub 145 is provided with two strips 12. The strips may extend from the same side of a hub, as illustrated in FIG. 36B or extend in opposite directions as illustrated in FIG. 36A. The disposable cuffs could include a tag with such information as, but not limited to, the time/date of the arrest, crime committed, arresting officer, etc, tying a face, and/or fingerprints to an identification band by software (not shown). In other embodiment, a chip for information storage or a capacitor to deliver a shock to a prisoner is provided (not shown). As further illustrated in FIG. 37, a pressure column device, or field dressing, is provided, where the multi hub 145 is used to apply pressure to a wound. As illustrated the linkage device is used around a leg, such as the right leg 285 while the second strip immobilizes a second, or left, leg 286.

Figure 48:
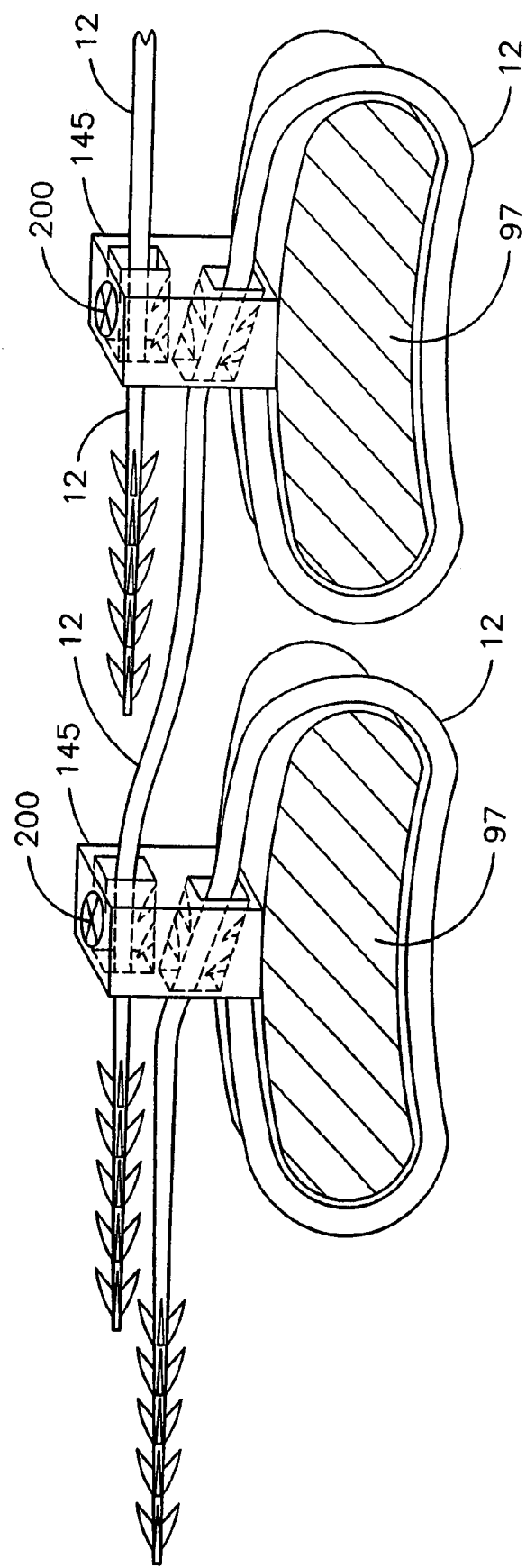
FIG. 48 is an illustration of an exemplary embodiment a cross sectional view of linkage devices used as braces to correct teeth alignment.

In another preferred embodiment, illustrated in FIG. 48, the linkage devices are used as braces to correct teeth. As illustrated, a multi-hub 145 is used where a strip 12 is wrapped around a tooth 97 and then is inserted through the hub 145. The strip is then inserted to an adjoining hub 145 connected to an adjacent tooth. A torque screw 200 is connected to the hub 14 to secure the strips in place. In a preferred embodiment the torque screw 200 does not adjust its own strip, but instead adjusts tension on the strip attached to the adjacent tooth. In another embodiment, not shown, two torque screws are provided on a hub to adjust each strip.

Figure 39:
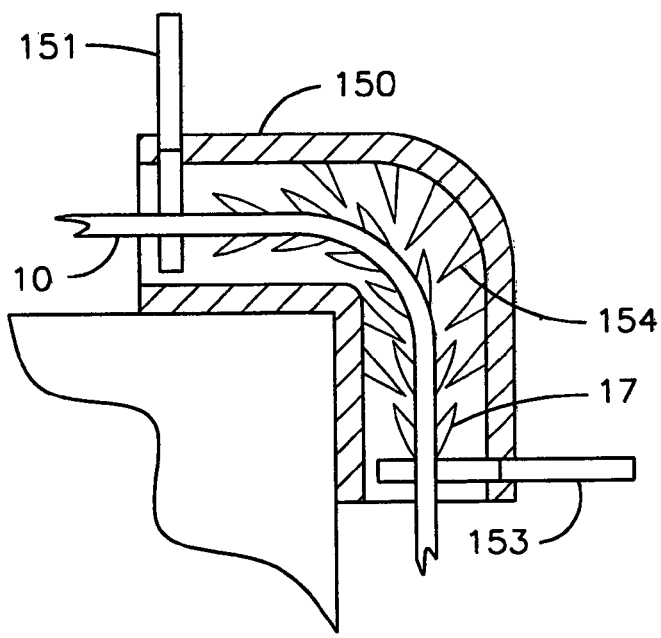
FIG. 39 is an illustration of an exemplary embodiment of a corner tab.

In another preferred embodiment, when using the linkage device to secure packages, instead of using glue on the back of the invention to hold the invention in place, corner tabs 150 placed at the edges of the container and the linkage device 10 is fed through an opening in the corner tabs 150, as illustrated in FIG. 39. The protrusions 17 on the linkage device will then engage protrusions 154 on the inner surface of the corner tabs 150, preventing the presenting invention from slipping. In another preferred embodiment, the stopper ends 151, 153 of the corner tabs 150 are pressed in toward the container thus providing a further block to any slippage of the linkage device 10 by acting as a stiff restraint to the reverse motion of the device by engaging the protrusions 17.

Figure 41:
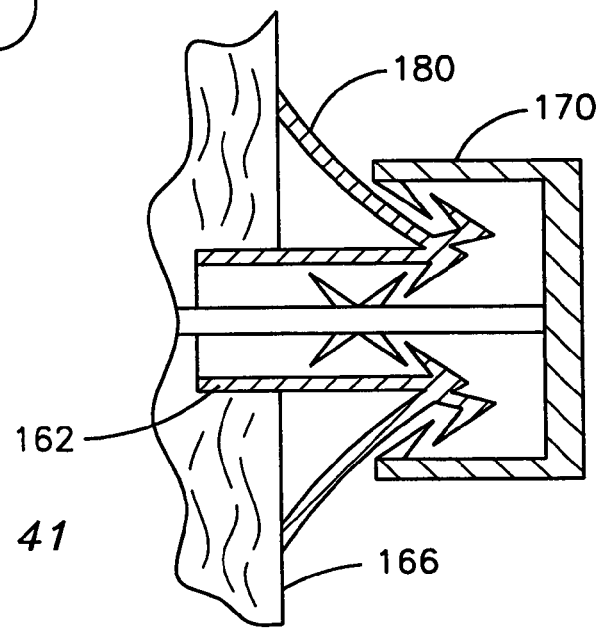
FIG. 41 is an illustration of an exemplary embodiment of an external cortical anchor (in the bone) end of the linkage device.

Referring again to medical uses, the linkage device can be used to replace a tendon in a knee, such as when an anterior and/or posterior cruciate ligament (ACL or PCL, respectively) injury occurs. In a preferred embodiment, as illustrated in FIGS. 40 and 41, a tunnel 160 is drilled into the femur 165 and tibia 166 so that the linkage device is positioned in the location that the ACL or PCL should be located. The tunnel 160 in the tibia 166 starts slightly wider and grows smaller so that the external cortical hub 14 will fit snuggly within the tibia 166. Similarly, the end where the linkage device 10 exits the femur 165 has a hole 162 that is large enough to accommodate the fixed cortical hub 180 it inserts into, as illustrated in FIG. 41. In another preferred embodiment the linkage device 10 could be inserted into the disc, attached to a hub (not shown). Once the linkage device is pulled through, a hub 170 is pushed onto a fixed device in the cortical 180 which can accept the hub or strip of the device as needed. To show this anchor, as illustrated in FIG. 41, the anchor 180 is fitted within a hole 162 where the anchor 180 has a connection point which holds a linkage device in place by way of its hub 170, or second end 15 (not shown). One skilled in the art will realize that the hub 170 can be placed in the tibia 166 and the second end 15 passes through the femur 165. These holes can be smaller than the tunnels currently used for native ligament repairs.

Figure 42:
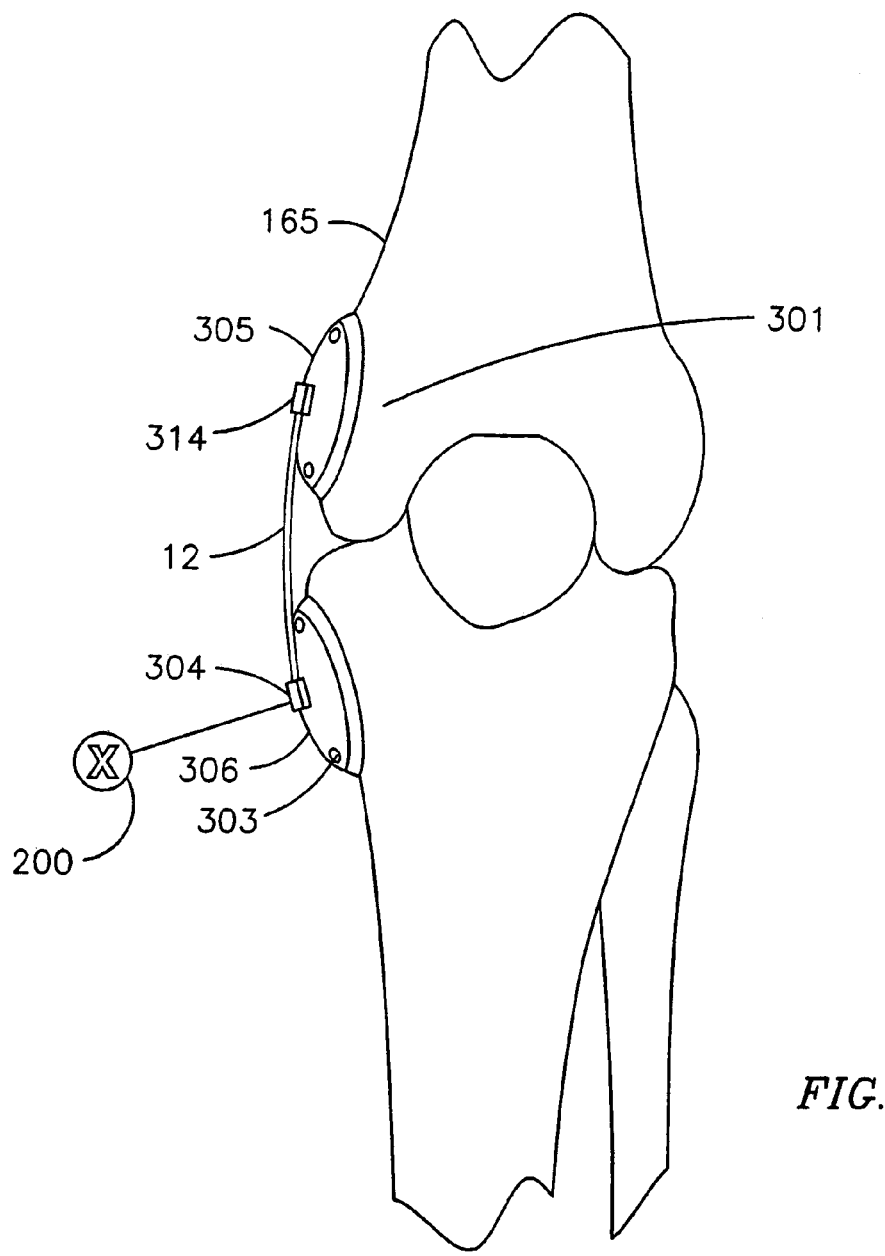
FIG. 42 is an illustration of an exemplary embodiment of the linkage device secured to a tibia and femur to replace a medial collateral ligament MCL.

As further illustrated in FIG. 40, cortical discs 218 are provided to anchor the strip 12 much as the anchor 180 are dclosed with respect to FIG. 41 and FIG. 42. In another preferred embodiment, illustrated in FIG. 47, when the drill insertion device 62 is used, the drill bit 60 remains in the femur as the superior anchor with one end, the hub end, of the linkage device 10 connected to the bit and the other end 15 is secured by the external cortical bone anchor 218 outside of the tibia 166, or an implanted anchor 162 (not shown). There can be a torque screw 200, not shown, to tighten the artificial ligament as needed at the external end of the strip 12 as it exits the cortical disc 218.

As is fully illustrated herein, a plurality of uses for the linkage device is available. FIG. 42 is an illustration of an exemplary embodiment of the linkage device used to repair a ruptured medial collateral ligament. As illustrated a plate, anchor, or saucer, 305 is secured to the medial condyle of the femur. 301. In a preferred embodiment screws 303 are used to secure the plates, or anchor, 305, 306 to the bone. A hub 304 is fixed to one plate 306 and a hub 314 with a strip is fixed to the second plate 305. Once the plates 305, 306 are in place, the strip 12 is inserted into the second hub 304 until a predetermined tension is achieved. A tension screw 200 can modify this tension.

Figure 43:
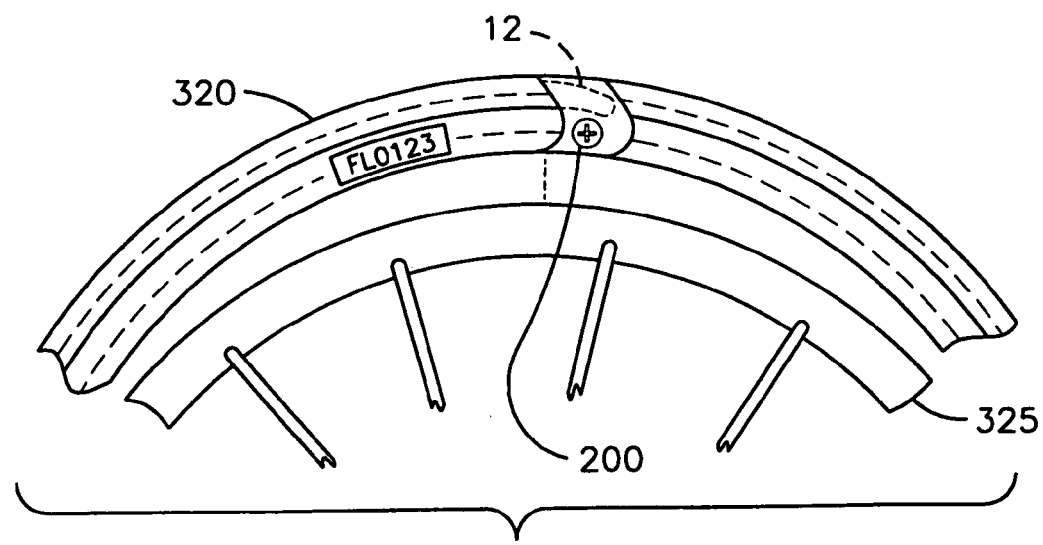
FIG. 43 is an illustration of an exemplary embodiment of a linkage device used as a replacement bicycle tire.

In another embodiment, illustrated in FIG. 43, the insertion hub is a replacement tire, or belt 320, such as for a bike, and the strip 12 connects the hub until its two facing surfaces are flush or a minimum gap is left. In a preferred embodiment, an adjustable torque screw 200, discussed above, is used to further secure the replacement tire 320 to a rim 325. In another preferred embodiment, not shown, the linkage device is used as an emergency fan belt where the strip connects to the hub after being placed around its respective pulleys and then is tightened by the adjustable torque screw.

While the invention has been described in what is presently considered to be a preferred embodiment, many variations and modifications will become apparent to those skilled in the art. Accordingly, it is intended that the invention not be limited to the specific illustrative embodiment, but be interpreted within the full spirit and scope of the appended claims.

What I claim is:

1. A linkage system, said system comprising:
(a) linkage device comprising a strip, a closure hub attached to a first end of said strip and having an opening to receive a second end of said strip and a locking mechanism within said closure hub to hold said second end where said second end cannot be pulled out of said opening without user authorization, a connecting surface on said strip operable to secure said second end within said closure hub;
(b) a tampering detection device; and
(c) an insertion device for simultaneously moving said at least one linkage device around an object, said insertion device being moved relative to said object, and wherein said at least one linkage device is detachable from said insertion device once said at least one linkage device is in place around said object;
(d) wherein said insertion device comprises a first handle, a second handle, a needle, a connection rod between said first handle and said second handle to secure said needle, and a dilator comprising a first end and a second end wherein said first end is connected to said needle and said second end is connected to a second end of said at least one linkage device.

2. The system of claim 1 wherein said insertion device comprises a plurality of needles and dilators wherein said connection rod comprises a plurality of needle attachments and each needle is at an adjustable distance from each other needle along said connection rod.

3. The system of claim 1 wherein said at least one linkage device further comprises an application distinct tag signifying a specific use for said at least one linkage device.

4. The system of claim 1 wherein said at least one linkage device is X-ray and MRI imaging compatible.

5. The system of claim 1 wherein said at least one linkage device further comprises at least one of an antibiotic medicine, an anti-fungal medicine, a bacteriostatic coating, a bactericidal coating, biologically active molecule that elutes into extra cellular spaces surrounding the linkage device, chemotherapeutic drugs, white cell chemotaxins, bone growth stimulants, and bone destructing inhibitors.

6. The system of claim 2, wherein said connection rod is separated into a top and bottom piece, said needle is passed between said separated top and bottom pieces, and said top and bottom pieces are joined to secure said needle between said top and bottom pieces.

7. The system of claim 6, wherein said top and bottom pieces are joined by passing at least one fastener through said top and bottom pieces.

8. The system of claim 2, wherein said adjustable distance of said plurality of needle attachments is adjusted based upon at least one dimension of a said object.

9. The system of claim 8, wherein said object is a rib of a patient, and said at least one dimension is a rib interspace of said rib.

10. The system of claim 2, wherein said first and second handles are configured to be held by a medical worker such that said plurality of needles are inserted into an intercostal space of a patient on an opposite side of a sternum of the patient from the medical worker.

11. The system of claim 10, wherein said first and second handles are configured to be rotated such that said plurality of needles are inserted through a muscle layer of said patient, wherein upon said plurality of needles having been inserted through said muscle layer, said insertion device is configured to be pulled towards said medical worker.

12. The system of claim 11, wherein upon said insertion device being pulled towards said medical worker, said plurality of needles are protruded through an intercostal interspace on a near side of said sternum of said patient from said medical worker.

13. The system of claim 12, wherein said plurality of needles are pulled through said intercostal space, such that each needle is subsequently threaded through said closure hub of said at least one linkage device.

14. The system of claim 3, wherein said application distinct tag is positioned on said closure hub.

15. The system of claim 14, wherein said application distinct tag is visible by photon activation of said specific use for said linkage device, said photon activation including one of laser, radio frequency photons, X-ray photons, gamma-ray photons, ultraviolet photons, and infrared photons.

\* \* \* \* \*